(12) United States Patent
Weibel

(10) Patent No.: US 10,603,428 B2
(45) Date of Patent: Mar. 31, 2020

(54) DEVICE FOR DISPENSING A FLUID TO A PATIENT

(71) Applicant: WEIBEL CDS AG, Waldstatt (CH)

(72) Inventor: Ludwig Daniel Weibel, Waldstatt (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 29 days.

(21) Appl. No.: 14/894,114

(22) PCT Filed: May 30, 2013

(86) PCT No.: PCT/EP2013/061153
§ 371 (c)(1),
(2) Date: Nov. 25, 2015

(87) PCT Pub. No.: WO2014/191038
PCT Pub. Date: Dec. 4, 2014

(65) Prior Publication Data
US 2016/0121043 A1    May 5, 2016

(51) Int. Cl.
*A61M 5/142* (2006.01)
*A61M 5/148* (2006.01)
*A61M 5/158* (2006.01)

(52) U.S. Cl.
CPC ........ *A61M 5/14216* (2013.01); *A61M 5/148* (2013.01); *A61M 5/158* (2013.01);
(Continued)

(58) Field of Classification Search
CPC .. A61M 5/14216; A61M 5/148; A61M 5/158; A61M 2005/14252;
(Continued)

(56) References Cited

U.S. PATENT DOCUMENTS

| 6,659,978 B1 | 12/2003 | Kasuga et al. |
| 2003/0135159 A1* | 7/2003 | Daily ................ A61M 5/14248 604/141 |

(Continued)

FOREIGN PATENT DOCUMENTS

| AU | 2010 207 762 A1 | 9/2010 |
| CN | 1747683 A | 3/2006 |

(Continued)

OTHER PUBLICATIONS

Chinese Office Action issued in corresponding Chinese Patent Application No. 201380078543.9 dated Sep. 29, 2019.
(Continued)

*Primary Examiner* — Kevin C Sirmons
*Assistant Examiner* — Tezita Z Watts
(74) *Attorney, Agent, or Firm* — Davis & Bujold PLLC; Michael J. Bujold

(57) ABSTRACT

A device (1) for dispensing a fluid, in particular to a patient, comprising a container (15), in particular an at least partly collapsible container, with an interior (17) for receiving the fluid. The container (15) comprises a closure piece (20) which is rigidly arranged in the container (15) in particular and on which a dispensing opening (24) is formed, wherein the fluid can be dispensed out of the interior (17) through the dispensing opening. The device (1) comprises a pump device (40) driven by a pump drive (50) in order to pump the fluid out of the interior (17) of the container (15). The pump device (40) is fluidically arranged between the interior (17) and the dispensing opening (24) so that the fluid can be pumped out of the interior (17) to the dispensing opening (24) by the pump device (40).

16 Claims, 18 Drawing Sheets

(52) U.S. Cl.
CPC ............ *A61M 2005/14252* (2013.01); *A61M 2005/1585* (2013.01)

(58) Field of Classification Search
CPC ...... A61M 2005/1585; A61M 25/0606; A61M 2005/3284
See application file for complete search history.

(56) References Cited

U.S. PATENT DOCUMENTS

| | | | |
|---|---|---|---|
| 2004/0010207 A1* | 1/2004 | Flaherty | A61B 5/14532 600/573 |
| 2008/0215006 A1* | 9/2008 | Thorkild | A61M 5/14248 604/151 |
| 2009/0204077 A1 | 8/2009 | Hasted et al. | |
| 2009/0292245 A1 | 11/2009 | Basso et al. | |
| 2010/0130932 A1* | 5/2010 | Yodfat | A61M 5/14248 604/151 |
| 2011/0043357 A1* | 2/2011 | Peatfield | A61M 5/1413 340/522 |
| 2011/0098652 A1* | 4/2011 | Hasted | A61M 5/14248 604/174 |
| 2014/0031793 A1* | 1/2014 | Constantineau | A61M 5/14248 604/510 |
| 2014/0058360 A1* | 2/2014 | Schoonmaker | A61M 25/0606 604/510 |

FOREIGN PATENT DOCUMENTS

| | | |
|---|---|---|
| CN | 101027094 A | 8/2007 |
| CN | 101687075 A | 3/2010 |
| CN | 101951977 A | 1/2011 |
| WO | 02/40083 A2 | 5/2002 |
| WO | 03/090509 A2 | 11/2003 |
| WO | 2008/040478 A1 | 4/2008 |

OTHER PUBLICATIONS

International Search Report Corresponding to PCT/EP2013/061153 dated Feb. 21, 2014.
Written Opinion Corresponding to PCT/EP2013/061153 dated Feb. 21, 2014.

* cited by examiner

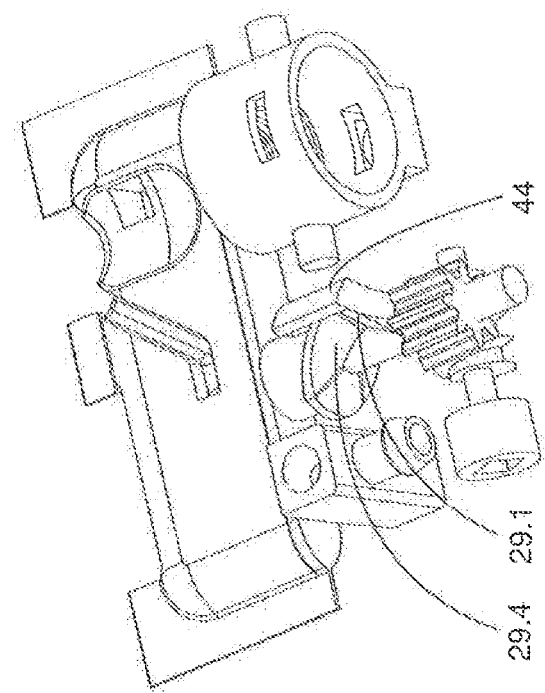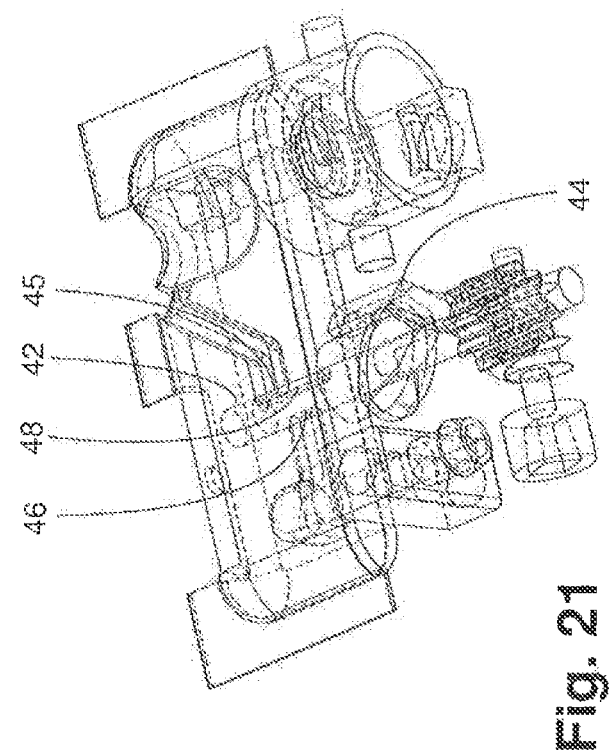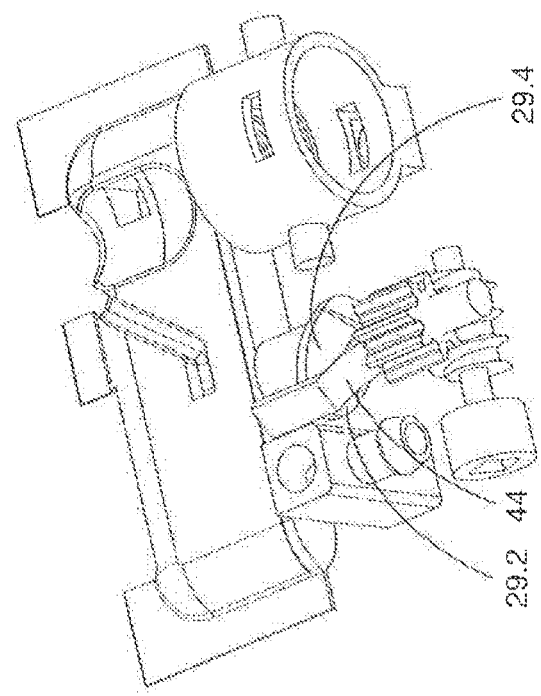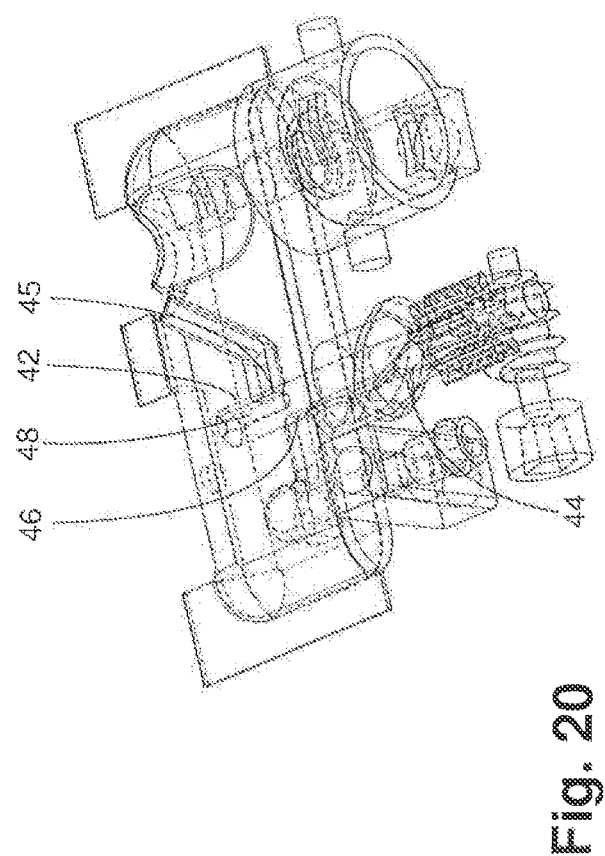
Fig. 20
Fig. 21

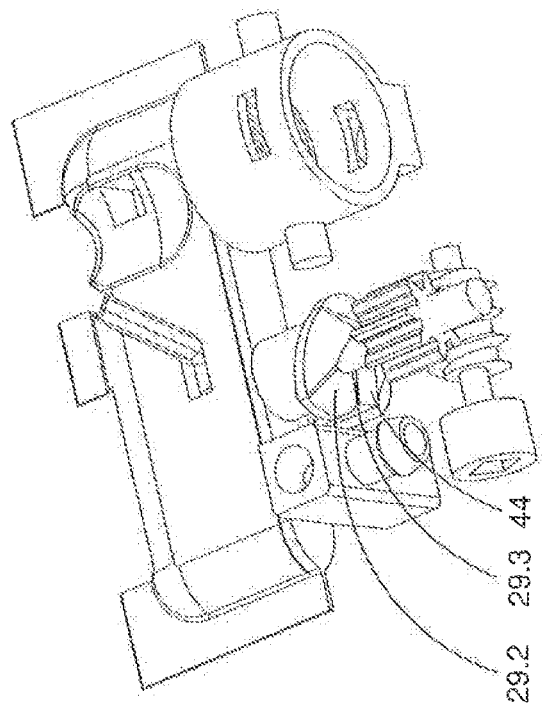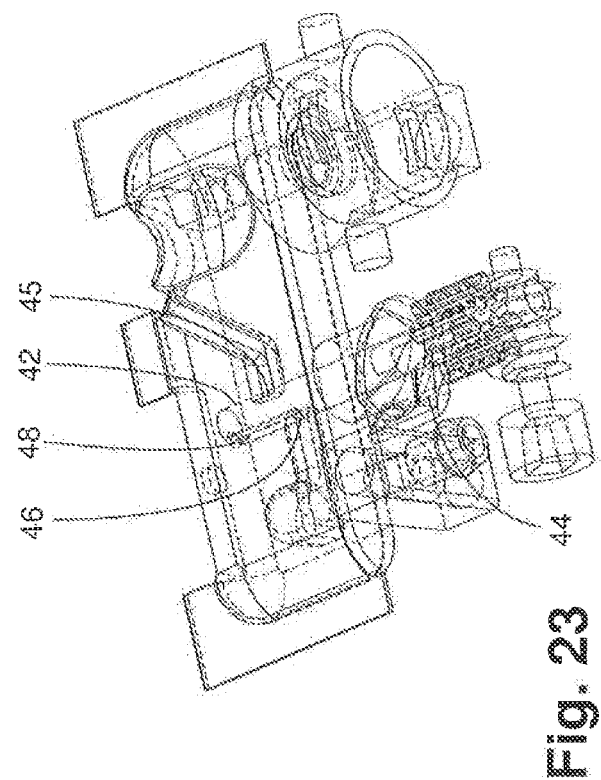
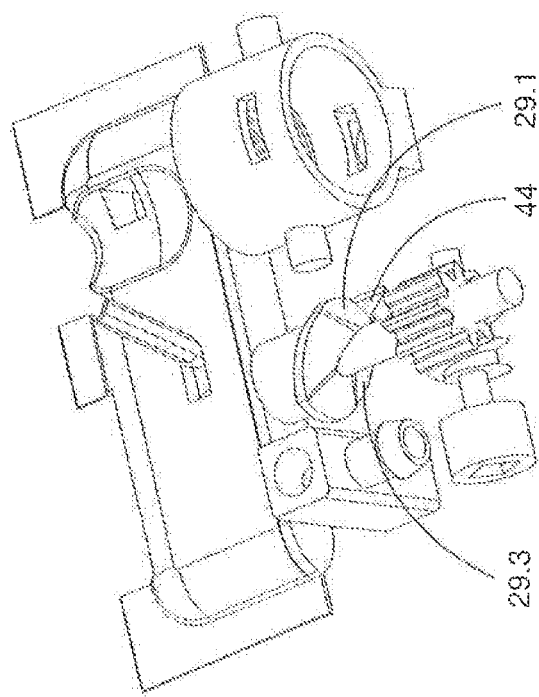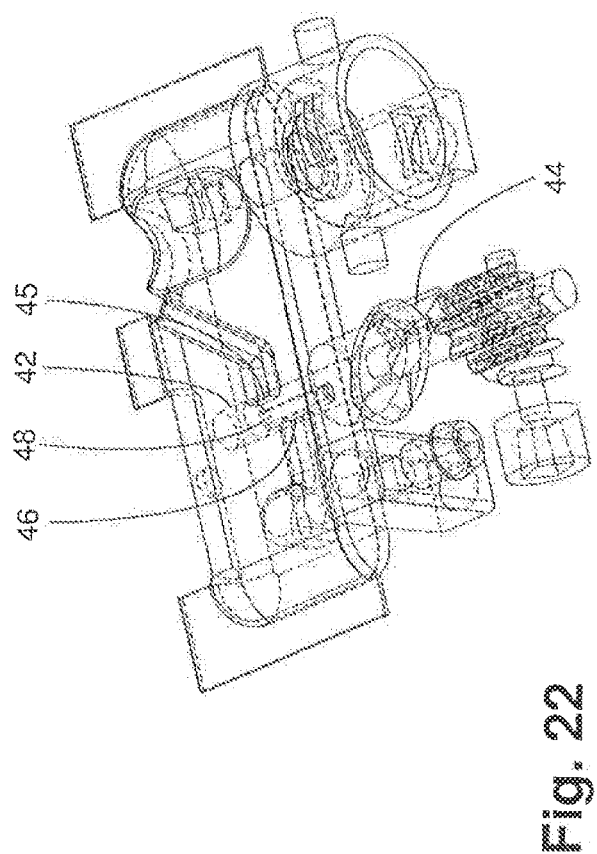
Fig. 22
Fig. 23

DEVICE FOR DISPENSING A FLUID TO A PATIENT

The invention relates to a device for dispensing a fluid, in particular to a patient, as per the preambles of the independent claims.

For the administering of liquid medicines, it is often necessary to dispense very accurately dosed small amounts of the medicine. Here, it is often necessary for the medicine to be injected into the body of a patient. This is the case in particular in the case of medicines which entirely or partially lose their effect if administered orally. Such medicines include in particular proteins (for example insulin, growth hormones, interferons), carbohydrates (for example heparin), antibodies or most vaccines. For parenteral injections, use is made of injection syringes, medicine pens, or medicine pumps.

Whereas injection syringes provided for single use have certain advantages owing to the low maintenance outlay and worldwide availability, they nevertheless require a certain level of experience on the part of the user for error-free application. In particular, the medicine must possibly be drawn out of corresponding ampoules, wherein, for example, it is necessary to ensure adequate absence of bubbles and to ensure sterile conditions. This is awkward in particular for patients with diabetes, who must often administer an insulin dose several times per day under greatly fluctuating conditions.

Therefore, in the case of medicines that most be administered at regular intervals, injection syringes are increasingly being replaced by so-called medicine pens. Medicine pens have the advantage that an exchangeable medicine container (for example ampoule, carpoule), comprising an adequate amount of medicine for several doses, is inserted directly into the medicine pen. Such containers may for example be pre-filled and shipped in a sterile state. When the container is inserted, a fluidic connection is produced between the medicine pen and the container. For the administering process, by way of an injection mechanism, a predefined amount of the medicine is extracted in each case from the container, for example by way of a piston rod, and administered. Such medicine pens often require increased care when changing the medicine container, as the injection mechanism must be reset into a starting position. Furthermore, there is the risk of mechanical malfunction, as such medicine pens are often used daily and must be carried by the user, for example in a pocket.

Medicine pumps are designed to be affixed to the body of the patient for relatively long periods of time (see for example WO 2008/04078 A1). Such medicine pumps typically comprise a container for the liquid medicine and also a pump which delivers the medicine to a port of the device or to an injection system. The injection system may in this case comprise an indwelling cannula which remains in the body of the patient throughout the entire administering period.

Medicine pumps have the advantage that the medicine can be dispensed continuously in small amounts, and thus differ fundamentally from injection syringes or medicine pens such as for example insulin pens with individual dispensing operations at fixed points in time. However, it is often the case that the desired reliability of the pump is not ensured with adequate safety, or the accuracy of the dispensed medicine amount does not correspond to medical requirements. Furthermore, the application of the indwelling cannula often requires a certain level of experience on the part of the user, and there is the risk of a fluidic connection between the medicine pump and indwelling cannula being disrupted.

To make the application of the indwelling cannula simpler and comfortable, various known medicine pumps have integrated injection devices (see for example WO 2003/090509 A2). Here, the indwelling cannula is automatically applied by a drive when the device is put into operation. The soft indwelling cannula is in this case often supported by a hard puncture tip which is deployed for application purposes and is retracted again. The hard puncture tip serves to penetrate the skin of the patient. The soft indwelling cannula remains in the patient when the puncture tip has been retracted.

While such injection devices already offer very high user comfort, conventional injection devices often have a non-uniform puncture movement, whereby the application of the indwelling cannula can be painful. Furthermore, there is the risk of the indwelling cannula being damaged during the application process, in particular by the hard puncture tip, for example if the latter strikes the inner wall of the indwelling cannula during the retraction movement.

Since such medicine pumps are worn on the body over a relatively long period of time, there is a general requirement for both the injection device and the further elements of the medicine pump, in particular the pump itself, to be of highly robust design. Owing to the often life-sustaining function of the dispensing of the medicine, there are also increased demands on reliability of the device during operation. Owing to the required miniaturization and the customary at least partial design as disposable units, the need exists to provide the simplest possible construction.

It is therefore an object of the invention to overcome the disadvantages of the prior art. In particular, it is an object to provide a device for dispensing a fluid to a patient, which device is both reliable and is also robust and comfortable to handle. Furthermore, the device should have a simple construction and should be inexpensive to produce.

Said objects are achieved by means of a device having the features of the independent claims.

One aspect of the invention relates to a device for dispensing a fluid, in particular to a patient, comprising an in particular at least partially collapsible container with an interior space for accommodating the fluid. The container comprises a closure piece which is in particular arranged fixedly in the container and on which there is formed a dispensing opening via which the fluid can be dispensed from the interior space. The device comprises a delivery device which is driven by a delivery drive and which serves for delivering the fluid out of the interior space of the container. The device is characterized in that the delivery device is arranged fluidically between the interior space and the dispensing opening, such that the fluid can be delivered from the interior space to the dispensing opening by means of the delivery device.

Here, a "fluidic arrangement" refers to an arrangement in the sense of interaction of the components by fluid communication. A "fluidic arrangement" of an element between two components thus has at least one fluid path which leads from one component to the other via the element.

In the present case, the delivery device is arranged fluidically between the interior space of the container and the dispensing opening of said container, which is formed on the closure piece. In this way, the delivery device may be formed entirely or partially on the container, in particular in the closure piece. The delivery drive may be arranged outside the container, and may be coupled, or able to be coupled, to the delivery device for example by a coupling means. Solutions are however basically also conceivable in which the delivery device can be coupled to the container in order to realize the fluidic arrangement according to the invention between the interior space and the dispensing opening.

The closure piece may be utilized for the integration of parts of the delivery device into the closure piece. Here, it is for example the case that no connections, or only a few fluid-tight connections, which may be susceptible to leakage need to be formed. With suitable design, the device may for example require only one fluid-tight connection, which for example connects the dispensing opening of the container to an injection device for, for example, subcutaneous administering of the fluid.

Any provided fluid ducts which connect the interior space and/or the dispensing opening to the delivery device may likewise be formed in the closure piece. The closure piece may therefore be formed, for example, as a unipartite injection-molded part in which, for example, parts of the delivery device, and/or fluid ducts and fluid openings adjoining these, may be formed so as to be fixedly connected to one another. In this way, it is possible for fluid-conducting components to be integrated into the container, whereby for example a structural size of the device can be reduced, and reliability can be increased.

An at least partially collapsible design of the container has the advantage that no ventilation openings have to be provided in order to compensate for a negative pressure, which arises owing to the extraction of the fluid, by way of a replenishing flow of air into the container. Furthermore, collapsible containers such as for example pouches can be of flat form, which yields a space-saving arrangement in particular in the case of portable devices.

The delivery drive may be designed to be couplable to the delivery device, such that a drive unit may be designed so as to be separable from a dispensing unit of the device. This may be advantageous for example in the case of portable insulin dispensing systems, in which the drive unit, as a reusable module, can be coupled to in each case unused dispensing units. The drive unit preferably also comprises an energy store for the delivery drive and also a control unit for the delivery drive and/or for controlling the device. Likewise, in the drive unit, there may be provided communication means by which, for example, an external operating unit can be connected to the control unit.

In the closure piece of the container there may be formed an extraction duct which communicates with the interior space and which fluidically attaches to the delivery device. Likewise, in the closure piece, there may be formed a dispensing duct which communicates with the dispensing opening and which attaches to the delivery device. The attachment to the delivery device is self-evidently designed such that the fluid can be delivered via the extraction duct from the interior space into the dispensing duct, and to the dispensing opening, by the delivery device. In variants, the delivery device may also attach directly to the interior space, for example to an extraction opening in the closure piece, and/or may directly adjoin the dispensing opening. The delivery device is preferably designed such that the fluid can be extracted from the interior space, in particular via the extraction duct, by suction.

For a simplified construction, the delivery device may be in the form of a valveless positive-displacement pump. A design without valves is particularly easy to implement in terms of construction, which is advantageous in particular in the case of a high level of miniaturization, such as is encountered for example in portable insulin dispensing systems.

The valveless positive-displacement pump may for example comprise a rotary piston pump. The valveless positive-displacement pump is however preferably in the form of a wobble piston pump with a piston and with a stroke chamber, wherein the piston, during every stroke movement in the stroke chamber during operation, performs a rotational movement about an axis running in the stroke direction. Such wobble piston pumps have a particularly simple construction and can therefore be of lightweight and compact form. In this way, the pump can be at least partially or entirely integrated into the container and may for example be formed in the closure piece. Furthermore, wobble piston pumps can exhibit high dosing accuracy and can be operated in any orientation with respect to a direction of gravitational force, which is advantageous in particular in the case of portable insulin dispensing systems. With the change in drive direction, the inlet/outlet direction can be reversed. Furthermore, no valves are necessary, because supply and discharge openings into and out of the stroke chamber can be closed by the piston itself owing to its rotational movement performed during the stroke movement. The piston thus generally forms the only moving part of the pump.

The piston comprises, on the circumference, a cutout which is open on the face side and which places the respective supply or discharge opening in fluid communication with the displacement chamber, defined by the piston, in the stroke chamber. The cutout may for example be in the form of a flattened portion on the shell of the piston. The cutout is however preferably in the form of an axially oriented longitudinal channel on the shell surface of the piston. In this way, it is possible for multiple azimuthally adjacent supply openings and dispensing openings in the stroke chamber to be operated in targeted fashion by virtue of the longitudinal channel communicating with in each case one of the feed openings or one of the dispensing openings depending on the rotational position of the piston. A width of the longitudinal channel in the circumferential direction is in this case preferably dimensioned such that the openings can be at least completely overlapped by the longitudinal channel.

An axial length of the recess is generally predefined by the stroke and the axial arrangement of the openings. It is preferably possible, when the piston is pushed in fully, for at least one of the openings to communicate with the cutout when the piston is situated in the corresponding rotational position. The cutout may, for improved sealing with respect to an inner wall of the stroke chamber, have a sealing rib which encircles the cutout or longitudinal channel at the shell side.

It is thus preferably provided that, in a manner dependent on a rotational position of the piston, the stroke chamber can be fluidically connected to the interior space, in particular possibly via the extraction duct, or to the dispensing opening, in particular possibly via the dispensing duct. Here, the extraction duct issues into the stroke chamber for example at the supply opening, whereas the dispensing duct issues into the stroke chamber at the discharge opening. It is self-evidently also possible for the supply opening to issue directly into the interior space, and/or for the dispensing opening to coincide with the discharge opening.

It is preferable for at least the stroke chamber of the wobble piston pump to be formed in the closure piece. In this way, it is for example also possible for fluid ducts which attach to the stroke chamber to be formed directly in the closure piece. Here, the piston advantageously projects into the stroke chamber from outside the closure piece.

In particular, in this way, it is possible for the piston of the delivery device to be mounted outside the container in the device, in particular on a housing of the device, so as to be rotatable about the axis running in the stroke direction and so as to be displaceable in the stroke direction. In this case, the delivery device comprises parts of the container, for example the stroke chamber, and parts outside the container, for example bearing arrangement of the piston or parts of the piston.

The delivery drive of the delivery device may comprise a rotary drive, in particular an electric rotary drive, by means of which the rotational movement of the piston can be generated. The stroke movement may in this case be realized for example by way of a gearing or a mechanical guide for control purposes, which gearing or mechanical guide converts the rotational movement at least partially into a stroke movement. Separate drives responsible for generating the stroke movement and the rotational movement are self-evidently likewise also conceivable. For example, the delivery drive may comprise a linear drive for the stroke movement and a rotary drive for the rotational movement. A separate stroke drive may, for example in the manner of a magnetic linear drive, be magnetically directly coupled to the piston.

It is self-evident that the rotary drive and/or further drives, and for example the piston itself, may be monitored by monitoring devices arranged in the device. In this way, it can for example be ensured that a present piston position corresponds to an expected position.

It may possibly be provided that the rotary drive can be or is coupled to the piston by way of a drive gearing, in particular comprising a worm gear. A worm gear allows, for example, a drive shaft extending from the drive to be arranged at an angle, in particular right angle, to the piston axis. In this way, the drive train can be adapted in a versatile manner to the space conditions.

Owing to the drive gearing, it is furthermore for example possible for a gearwheel which is fixedly connected to the piston to be displaceable relative to a further gearwheel, without meshing of the two gears being lost. This is advantageous in particular in the case of the presently superposed rotational and stroke movements of the piston. The drive gearing may furthermore additionally comprise control disks or other elements which control, for example, a movement of the piston.

The stroke movement of the piston is preferably coupled to the rotational movement of the piston. Here, the stroke movement is advantageously positively coupled to the rotational movement, wherein the coupling may be realized mechanically. In this case, the coupling is advantageously realized by way of a control surface which is formed in particular on the closure piece of the container. Here, a runner which is fixedly connected to the piston can slide on the control surface.

Other known types of mechanical couplings are self-evidently also conceivable. Owing to the positive coupling, it can be ensured in a simple manner that the piston, in every stroke position, is also situated in a desired rotational position, or vice versa.

The coupling may self-evidently also be realized electronically by way of a drive controller, in particular in the case of separate drives being provided for the stroke movement and rotational movement. It is also self-evidently possible, if necessary, for the stroke movement and rotational movement to be controlled independently of one another.

The closure piece of the container may have a filling duct which communicates with the interior space and which, at a filling opening of the closure piece, is open to the outside in closable fashion. In this way, the empty container can for example be inserted into the device and can be filled for the first time before the device is used by a user. It is self-evident that pre-filled containers may also be used, which, already filled with a fluid in the shipped state, are arranged in the device.

The filling opening may be equipped with a coupling means for the coupling of a fluid source, in particular a Luer coupling. In this way, the fluid source, such as for example a syringe or a reservoir, can be connected to the container in a simple manner. A housing of the device, and the filling opening, may for this purpose be correspondingly designed such that the filling opening is accessible from the outside. It is self-evidently also possible for the filling opening to comprise a medical self-sealing septum through which the fluid can be introduced into the container by way of an injection needle.

To prevent a return flow of the fluid out of the container, a valve device may be arranged in the filling duct. Said valve device may comprise a duckbill valve which blocks the filling duct with regard to a fluid flow from the interior space to the outside. Since the container is generally under positive pressure after the filling process, the duckbill valve closes with a sealing action which is adequate for most applications. Furthermore, for security, the filling opening may be closable by way of a plug in order to ensure that no fluid can emerge. Other valve devices are self-evidently also conceivable. For example, use may also be made of a valve device with two openings which are closed off by a sealing diaphragm that can be lifted off (see for example a valve device on a closure piece of a flexible container as per WO 2012/175465 A1).

It is self-evidently also possible for the filling opening to be closed in some other way. For example, a pouch foil of a container of partially collapsible form may be utilized to clamp off a filling duct, which is arranged under the foil, from outside the container. For this purpose, it is for example possible for a corresponding projection to be formed in the device, for example on the inside of a housing, which projection, when the housing is closed, presses against the pouch foil and clamps off the filling duct.

In general, it suffices for the container to have one interior space for at least one fluid. It is however self-evidently also possible for the container to be in the form of a multi-chamber container. In this case, the container comprises at least one further interior space which is separated from the first interior space such that at least one further fluid can be accommodated in the container separately from the first fluid. This may be necessary for example in the case of medicines which must only be mixed shortly before being administered. Likewise, it is basically conceivable for one of the interior spaces to comprise a medicine in solid form, for example in the form of a powder, whereas the other interior space comprises a solvent.

The delivery device is preferably arranged fluidically between the at least one further interior space and either the dispensing opening or at least one further dispensing opening or another of the interior spaces, in such a way that the at least one further fluid can be delivered by means of the delivery device from the interior space to the dispensing opening or to the at least one further dispensing opening or into the other of the interior spaces. The same delivery device can thus be designed for delivering the fluid between the interior spaces or between the interior spaces and one or more dispensing openings. This can be realized in a particularly simple manner in particular in the case of a swash-plate-action piston pump, as these can be formed with only one piston and one stroke chamber, as described above, in order to provide a supply to multiple adjoining ducts.

In the case of multiple dispensing openings being provided on the closure piece, it is for example possible for mixing of the fluids to take place for the first time outside the container. Likewise, it is for example possible for a separate injection system to be connected to each dispensing opening, which permits, for example, separate subcutaneous dispensing of the fluids from each interior space. If the fluid is delivered to the same dispensing opening, mixing may, depending on requirements, be performed for example in the container, or the fluids may be dispensed sequentially via the dispensing opening. For this purpose, it is possible for a static mixer to be provided for example at the dispensing opening or in the dispensing duct.

Alternatively, or additionally in the case of more than two interior spaces, it may be provided that, in the device, there is provided at least one further delivery device which is in particular substantially identical to the first delivery device and which is assigned to the at least one further interior space. The at least one further delivery device is in this case arranged fluidically between the at least one further interior space and the dispensing opening or at least one further dispensing opening or another of the interior spaces, in such a way that the at least one further fluid can be delivered by means of the at least one further delivery device from the at least one further interior space to the dispensing opening or to the at least one further dispensing opening or into the other of the interior spaces. The at least one further delivery device may thus be provided for delivering to one or more dispensing openings, or else exclusively for delivering a fluid between two of the interior spaces. The various possible combinations that arise on the basis of the additional delivery device are readily apparent. Owing to the possibility of integration of the delivery device into the container, in particular into the closure piece, the correspondingly required fluid ducts can all be formed in the closure piece or in the container itself (analogously to the case of the container with one interior space).

It is self-evidently also possible for multiple containers to be provided, wherein each container is assigned at least one delivery device. Here, the delivery devices may be of identical form. By virtue of each container being assigned at least one delivery device, it is however also possible for these to be of different design and adapted to the respective requirements, for example to the fluid contained in the associated container. The multiple containers may in this case be arranged in stacked form or adjacent to one another in the device.

In the case of multiple delivery devices, the rotational movements of the pistons of the delivery device are coupled, preferably mechanically. In this way, both delivery devices can be driven in a simple manner by way of only one delivery drive. The delivery devices may be operable synchronously or in a different ratio, for example by way of the correspondingly designed drive gearing. It is self-evident that the stroke movements may also be coupled, and that separate drives for stroke movement and rotational movement may also be provided for each of the delivery devices.

The device may comprise an injection device for continuous subcutaneous dispensing of the fluid, or possibly of the fluids, to the patient. This is advantageous in particular in the case of a design as, for example, a portable dispensing system for the subcutaneous administering of a liquid medicine, such as for example insulin. The injection device may comprise at least one injection cannula which, by way of an infusion hose, can be attached directly or indirectly to the dispensing opening of the container. Likewise, the device may also comprise at least one dispensing port which communicates with the dispensing opening and to which the injection system can be attached from outside the housing of the device.

Alternatively, the device may also be in the form of a static fluid source without an injection system and which, via a dispensing port, makes a fluid available for example in a precise dose. It is however preferable for the device to be designed as a portable dispensing system for the subcutaneous administering of a liquid medicine and to comprise an injection device which is integrated into the device and which, as-delivered, is arranged within a housing of the device.

A further aspect of the invention therefore relates, even independently of an embodiment or fluidic arrangement of the delivery device, to a device for dispensing a fluid, in particular to a patient, comprising a container for accommodating the fluid, having a housing which, on the outside, has a contact surface by way of which the device can be affixed to a body of the patient. Here, the device may be designed as described above. The device comprises an injection device which has a flexible transcutaneous indwelling cannula supported by a distal end region of a puncture cannula, wherein the puncture cannula is arranged in a readiness position substantially within the housing and, for the application of the indwelling cannula, said puncture cannula can, with the distal end region, be deployed out of the housing into an application position, and retracted into an end position again, through an application opening on the contact surface. A proximal end region of the puncture cannula is connected in fluid-tight fashion to a dispensing opening at which the fluid can be dispensed from the container. Here, a guiding device is provided, on which the distal end region of the puncture cannula is guided, preferably in displaceable fashion, during the in particular contact-free retraction and deployment through the application opening.

"Proximal" and "distal" relate each case to a relatively close (proximal) and relatively remote (distal) arrangement as viewed from the container with respect to the fluid flow during the dispensing.

The contact surface of the device preferably has an adhesive surface which allows the device to be affixed to the skin of the patient. For this purpose, the housing may exhibit flexibility in order to make the device more comfortable to wear. Likewise, the contact surface may have a curvature in order to ensure more comfortable abutment.

The puncture cannula is preferably designed to be stiff enough to be able to penetrate the skin of the patient. For this purpose, the puncture cannula has a puncture tip at its distal end. In the distal end region, the puncture cannula is encased by the indwelling cannula. The indwelling cannula is of flexible form and is composed of a biocompatible material of sufficient strength that it can remain in the patient as a transcutaneous cannula for a relatively long period of time. In the readiness position, the puncture tip of the puncture cannula protrudes beyond the indwelling cannula such that, during the application of the indwelling cannula, the puncture tip can penetrate the skin of the patient during the deployment movement.

The puncture cannula is, by way of its proximal end region, attached in fluid-tight fashion to a dispensing opening at which the fluid can be dispensed out of the container. In the end position, the distal end of the puncture cannula projects into the applied indwell in cannula, such that the fluid can be fed from the container to the indwelling cannula via the puncture cannula.

During the application of the cannula, during the deployment movement, the distal end region of the puncture cannula passes, together with the indwelling cannula arranged thereon, out of the device through the application opening. Here, owing to the guide device, the indwelling cannula can emerge through the application opening in substantially contact-free fashion, such that no folding-over of or damage to the indwelling cannula can occur at the application opening. During the retraction movement of the puncture cannula, the indwelling cannula remains in the deployed position. Here, the guide device ensures that the distal end region can be retracted counter to the puncturing direction, that is to say correspondingly to the position of the applied indwelling cannula, such that the puncture tip cannot damage the indwelling cannula.

It has been found that the application of the indwelling cannula is particularly comfortable if the distal end region is designed, and movable, such that, during the deployment and retraction, an outlet point is positionally fixed relative to the contact surface, and an outlet direction at the outlet point is constant with respect to the contact surface. It is ensured in this way that the distal end region penetrates the skin of the patient in a clean puncturing movement without lateral displacement. Here, the distal end region may be of curved form, wherein the puncture movement follows the curvature. It is likewise possible for the distal end region to be of rectilinear form, in which case the puncturing direction is rectilinear. The puncture movement preferably takes place perpendicular to the contact surface at least at the contact surface. It is readily apparent that, owing to the guide device according to the invention, the distal end region of the puncture cannula can be guided targetedly in the desired puncture movement regardless of a design of the application opening.

The guide device is preferably formed in the interior space of the housing. In this way, the guide cannot be jeopardized as a result of erroneous manipulation by a user.

The guide device preferably comprises a runner which, in particular in the distal end region, is rigidly connected to the puncture cannula and which is guided in displaceable fashion in a guide rail of the guide device. The guide rail may for example be in the form of curved guides on which the runner is guided displaceably on a curved path. Depending on the design of the distal end region, it is however also possible for the guide rail to be in the form of a linear guide.

The distal end region is preferably of rectilinear form, wherein the guide device is in the form of a linear guide. A rectilinear puncturing movement can be realized in a particularly simple and exact manner by way of the guide device. Likewise, a rectilinear form of the distal end region can be produced particularly easily. The guide device of the linear guide is preferably oriented perpendicular to the contact surface, and thus also perpendicular to the skin surface of the patient, giving rise, overall, to a perpendicular puncturing movement.

The proximal end region of the puncture cannula is advantageously oriented substantially parallel to the distal end region. Here, the ends of the puncture cannula preferably point in the same direction. In this way, it is possible to realize optimum usage of space for an extremely compact design of the device.

The puncture cannula may be in the form of a continuous hollow needle. Here, the puncture cannula is preferably manufactured from a steel. This has the advantage that a robust fluidic connection between the dispensing opening and the indwelling cannula can be pro vided without the need to additionally provide fluid-tight connections, for example with a flexible hose.

The proximal end region of the puncture cannula is preferably arranged in positionally fixed and rigid fashion in the device. This has the advantage that the puncture cannula can attach, or be attached, directly to the dispensing opening, which is arranged in positionally fixed fashion in the device. Thus, there is no need for unnecessary fluidic connections between puncture cannula and dispensing opening, which require additional seals and which are awkward with regard to leakage.

The puncture cannula preferably has, at least between the proximal end region and the distal end region, sufficient flexibility that the mobility of the distal end region required for the application can be provided, for example owing to bending of the puncture cannula. The guide device according to the invention ensures here that the bending of the puncture cannula does not have an influence on the puncturing direction of the distal end region.

Depending on the puncturing direction, in particular in the case of a rectilinear puncturing direction, length compensation may be necessary between the positionally fixedly arranged proximal end region and the distal end region. To provide adequate length compensation even in the case of a continuous puncture cannula, the puncture cannula may, at least in the readiness position, be of curved form in a central region between the proximal and the distal end region. Owing to the curved central region, adequate length compensation may be attained already by way of stretching or compression of the curved central region owing to a slight flexibility of the puncture cannula, for example in relation to the indwelling cannula, such as may exist for example in the case of steel. The puncture cannula preferably has a uniform direction of curvature in the central region. In other embodiments, it is self-evidently also possible for the direction of curvature to alternate, for example, such that the central region follows, for example, an undulating line. A curvature with a uniform direction of curvature is however generally easier to produce.

An angle enclosed between the proximal end region and an adjacent section of the central region and an angle enclosed between the distal end region and an adjacent section of the central region are preferably each less than 90 degrees. In this way, it is ensured that both the proximal, end region and the distal end region are sufficiently angled relative to the central region in order to provide the mobility of the distal end region required for application purposes in the case of a positionally fixed proximal end region.

The indwelling cannula may, as a whole, be arranged so as to be displaceable relative to the puncture cannula in the distal end region, wherein the indwelling cannula, at least in a proximal end region of the indwelling cannula, surrounds the puncture cannula in fluid-tight fashion with a sliding seal. It is ensured in this way that, during the retraction of the puncture cannula from the application position into the end position, the indwelling cannula can be at least partially pulled off the distal end region. When the indwelling cannula has been applied and the puncture cannula retracted, a fluid-tight connection between the puncture cannula and the indwelling cannula is ensured by way of the sliding seal. Alternatively, the indwelling cannula may be fixedly fastened by way of its proximal end region to the puncture cannula. In this case, the indwelling cannula may comprise an expandable or deformable region such as, for example, a bellows which, when the indwelling cannula has been applied, allows the distal end region of the puncture cannula to retract.

The indwelling cannula can preferably be in particular automatically arrested on the housing when the puncture cannula is in the application position. In this way, the indwelling cannula can, during the deployment movement, be automatically fixed in the application position, in particular on the housing. It is preferably possible for this purpose for a simple snap-action mechanism to be provided on the housing, in particular at the application opening, into which snap-action mechanism the indwelling cannula can engage with detent action. The indwelling cannula may for this purpose have, on its proximal end, an outwardly projecting detent collar.

During the retraction of the puncture cannula from the application position into the end position, the arrested indwelling cannula remains in the deployed, that is to say applied, position, and is at least partially pulled off the puncture cannula. In the end position, the puncture cannula projects by way of its distal end into the indwelling cannula and, owing to the sliding seal of the indwelling cannula, forms a fluid-tight connection to the indwelling cannula.

In the proximal end region of the puncture cannula, there may be formed a coupling means by which said puncture cannula is coupled to the dispensing opening, in particular possibly to the dispensing opening of the container. For example, a conical coupling piece may be formed on the puncture cannula, which coupling piece can be or is inserted into a corresponding seat at the dispensing opening. Alternatively, the puncture cannula may for example also be adhesively bonded into the dispensing opening by the closure piece of the container or the closure piece may be injection-molded around the puncture cannula.

An application drive is advantageously provided by means of which the distal end region of the puncture cannula can be deployed and retracted again by way of an application gearing for the purposes of applying the indwelling cannula. Here, the application drive and the application gearing are self-evidently designed such that the puncturing movement predefined by the guide device can be performed by the application drive. Embodiments are self-evidently also conceivable in which the application drive interacts directly with the puncture cannula, that is to say without an application gearing.

For this purpose, the application drive may comprise a rotary drive, and the application gearing may comprise a worm gearing. The rotary drive can be or is coupled to the puncture cannula, in particular possibly to the runner of the guide device, by way of the worm gearing. A rotary drive can, in a particularly simple manner, be provided for example by a commercially available electric motor. The worm gearing has the advantage that a gearwheel which is driven by the worm gear is also blocked by the worm gear. In this way, it is possible by way of the application gearing to ensure that the puncture cannula, once it has assumed a position, in particular the end position after the application of the indwelling cannula, is fixed in said position in self-locking fashion.

The application drive may also comprise a linear drive, and the application gearing may comprise a pivotably mounted knee lever, by way of which the linear drive can be or is coupled to the puncture cannula, in particular possibly to the runner of the guide device. A linear drive can be of particularly space-saving form and arranged in the device. The knee lever offers the advantage of a particularly simple diversion of a movement in a first direction into a movement into a second direction that differs from the first direction.

Alternatively, a linear drive may be provided for example by way of a simple electromagnet which, without a knee lever, acts directly on the runner of the guide device and, when activated, attracts said runner in order to deploy the puncture, cannula and, when deactivated, releases said runner. In this case, a restoring spring or a second linear drive may be provided in order to retract the puncture cannula into the end position. Likewise, the application gearing may for example also comprise a toothed rack which is movable in the direction of action of the linear drive and which engages into a gearwheel which interacts with the puncture cannula.

The application gearing may have a longitudinal guide, which is formed in particular possibly on the runner or on the knee lever and which is arranged substantially transversely with respect to the puncturing direction and into which a cam of the application gearing engages so as to be displaceable in the longitudinal guide. With this arrangement, a rotational movement can be converted into a linear movement in a particularly simple manner. The application gearing may for example have a rotary disk with an eccentrically arranged cam which engages into the longitudinal guide, which is in particular possibly formed on the runner. The rotary disk may, for example by way of a toothed ring formed on the circumference or by way of a gearwheel which is rigidly and coaxially connected to the rotary disk, be driven by a rotary drive, for example by way of a worm gear, or by a linear drive, for example by way of a toothed rack. In the case of a rotational movement of the rotary disk, the puncture cannula can be displaced in the guide device by way of the cam, wherein at the same time, the cam is displaced in the longitudinal guide. Since the cam reverses its movement direction in the puncturing direction during a rotation of the rotary disk, the retraction movement and the deployment movement can be performed with the same direction of rotation of the rotary disk.

It is for example likewise possible for the knee lever to possibly have said longitudinal guide, in which a cam, which is fixedly connected to the puncture cannula, is guided in displaceable fashion. If the knee lever is pivoted about its axis of rotation for example by a linear drive, it is for example the case that the cam displaces the puncture cannula in the guide device in the puncturing direction, wherein the longitudinal guide provides the required mobility of the cam.

It is self-evidently possible that, in all cases, monitoring devices may be provided, by means of which movable components, such as for example the application drive and/or the guide device, can be monitored. In this way, it can be ensured that a drive position or a position of the guide device and/or of the puncture cannula corresponds to an expected position.

In each embodiment, the device preferably comprises a drive module and a dispensing module which are designed such that they can be connected and separated from one another by a user. Here, the drive module comprises at least parts of the delivery drive, in particular possibly the rotary drive and/or possibly the application drive of the injection device. The dispensing module has at least the container and the delivery device and possibly the injection device. The drive module preferably also comprises a battery for providing a supply to the drives, and a control unit for controlling the device, in particular the drives. It is likewise possible for communication means to be provided in the drive module, by way of which communication means an external operating unit can be connected to the control unit.

The drive module and the dispensing module are preferably designed such that the drives can, by way of corresponding coupling means, be coupled in a simple manner directly or indirectly to the piston and/or to the injection system or to the drive gearing or to the application gearing. For this purpose, use may for example be made of positively locking and/or non-positively locking plug-type couplings. The drive module, which comprises hygienically non-critical components, may for example be designed to be reusable. The dispensing module, which comprises for example the hygienically relevant injection system and the fluid, may by contrast be in the form of a disposable module. The two modules can, for simple exchange, be coupled to one another and separated again for example by way of a snap-action coupling.

The invention will be discussed in more detail below on the basis of figures of exemplary embodiments, in which, in each case schematically:

FIG. 20 shows the delivery device in a first stroke of a pump cycle;

FIG. 21 shows the delivery device in a second stroke of the pump cycle;

FIG. 22 shows the delivery device in a third stroke of the pump cycle;

FIG. 23 shows the delivery device in a fourth stroke of the pump cycle;

Figure 1:
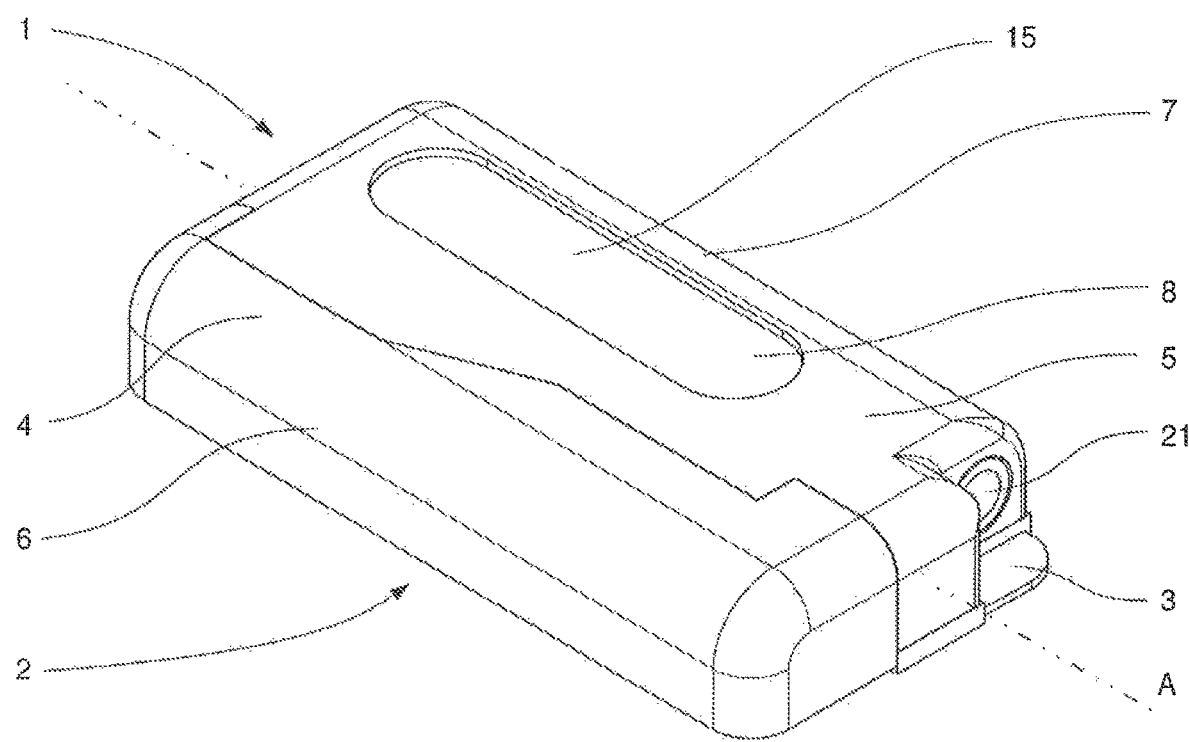
FIG. 1 shows a device accord in to the invention in an oblique view of a housing from above.
Figure 2:
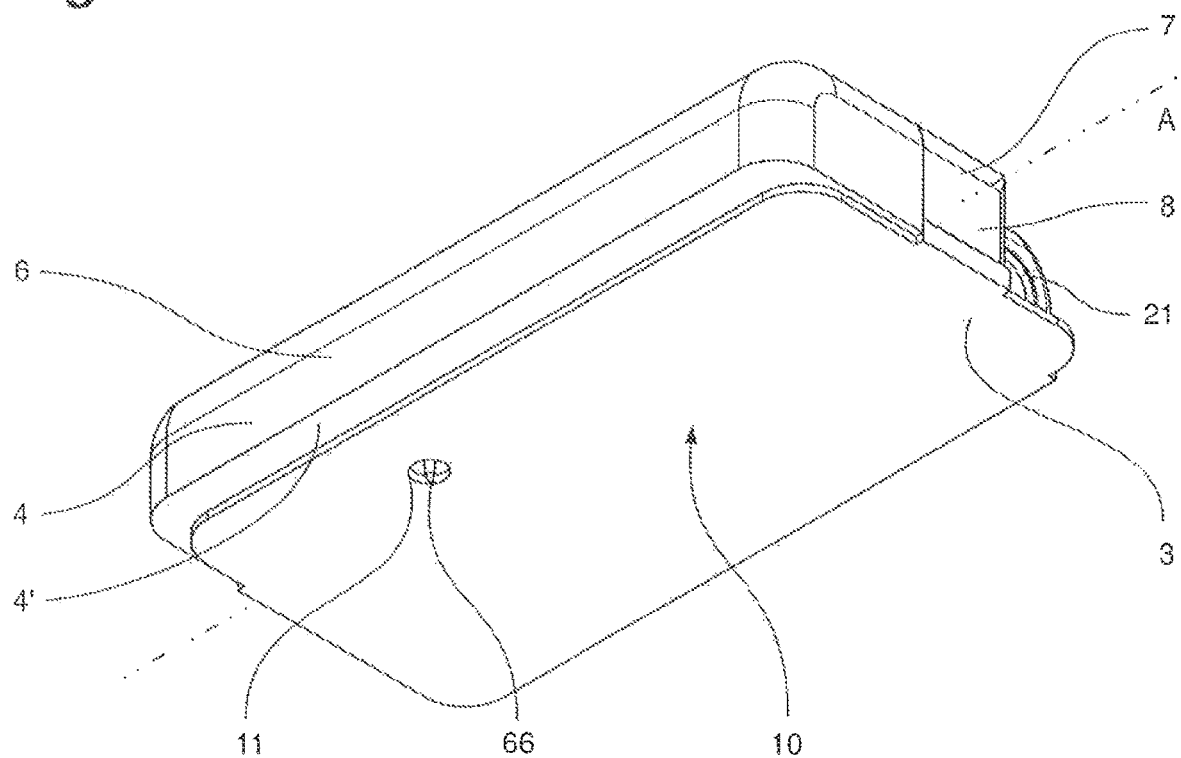
FIG. 2 shows the device as per FIG. 1 in an oblique view of a contact surface the housing from below.

FIG. 1 shows an external oblique view of a device 1 according to the invention from above, and FIG. 2 shows the same from below. FIGS. 1 and 2 will be described jointly below. The device 1 is in the form of a portable dispensing system for the subcutaneous administering of a fluid, in particular of a liquid medicine such as insulin.

The device 1 comprises a housing 2 which is of substantially cuboidal form with a longitudinal axis A and with rounded edges on the top side. The housing 2 has a continuous base plate 3 on which there are arranged two housing shells 4 and 5. Here, the housing shells 4 and 5 abut against one another in substantially flush fashion along parting surface, and together with the base plate 3 form the complete housing 2 of the device 1. The housing shells 4 and 5 are assigned to a drive module 6—housing shell 4—and to a dispensing module 7—housing shell 5. Owing to the separate housing shells 4 and 5, the drive module 6 and the dispensing module 7 can be separated from one another. The dispensing module 7 is formed as a disposable module, whereas the drive module 6 is reusable. The base plate 3 belongs to the disposable module 7, wherein, in the assembled state of the device 1, the drive module 6 is arranged on the base plate 3.

The housing shell 5 has a viewing window 8 through which the fill level of a container 15 arranged in the interior of the housing 2 can be inspected. On a face side on the housing shell 5 there is formed a filling port 21 which communicates with a filling duct 22 of the container 15 (see for example FIG. 17).

On the outside of the base plate 3 there is formed a contact surface 10 by means of which the device 1 can be affixed to the surface of the skin of a patient (not illustrated). In the present case, the contact surface 10 is of planar form. Below, an arrangement of the base plate 3 and a direction outward, away from the contact surface 10, will be referred to as being at the bottom/downward, whereas the housing shells 4 and 5 are arranged at the top.

For fastening to the surface of the skin, the contact surface 10 may have an adhesive layer. The device 1 can thus be adhesively bonded to the surface of the skin at a suitable location on the body of the patient, and can remain there for a relatively long period of time. On the contact surface 10 there is formed an application opening 11 through which an indwelling cannula 67 of an injection device 60 of the device 1 can be deployed for application purposes. Here, an opening plane of the application opening 11 lies in a plane of the contact surface 10.

Figure 3:
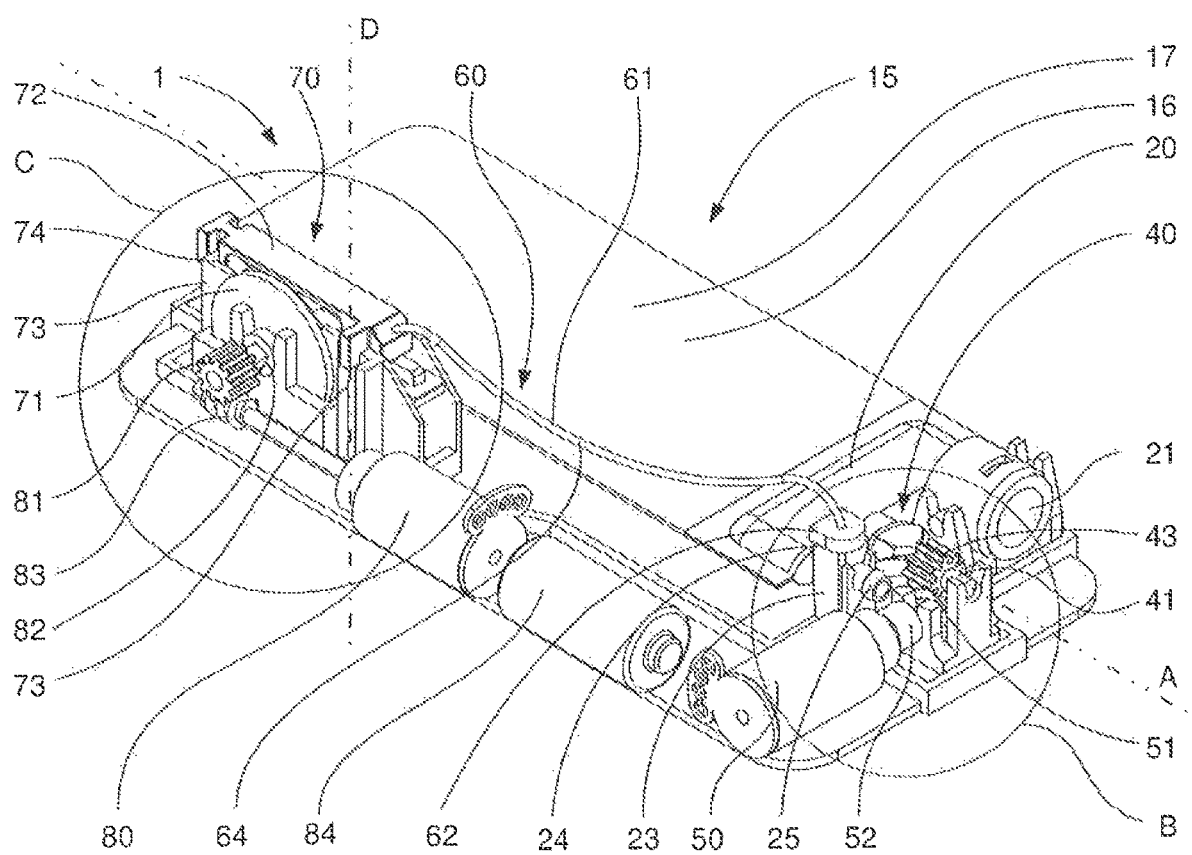
FIG. 3 shows an oblique view of the device of FIG. 1 without housing shells.
Figure 4:
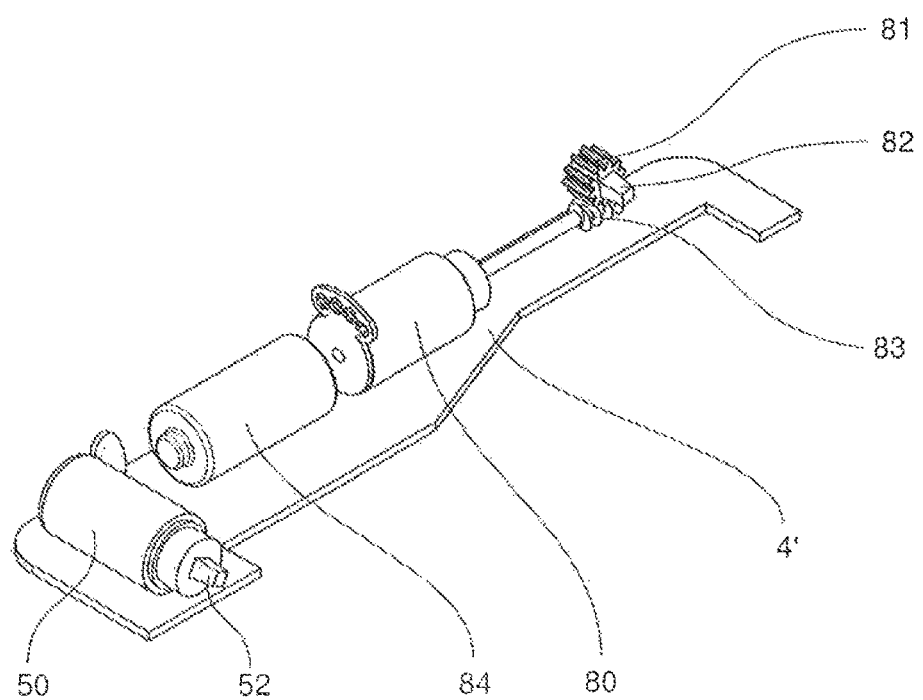
FIG. 4 shows a drive module of the device of FIG. 3 without an upper housing part.
Figure 5:
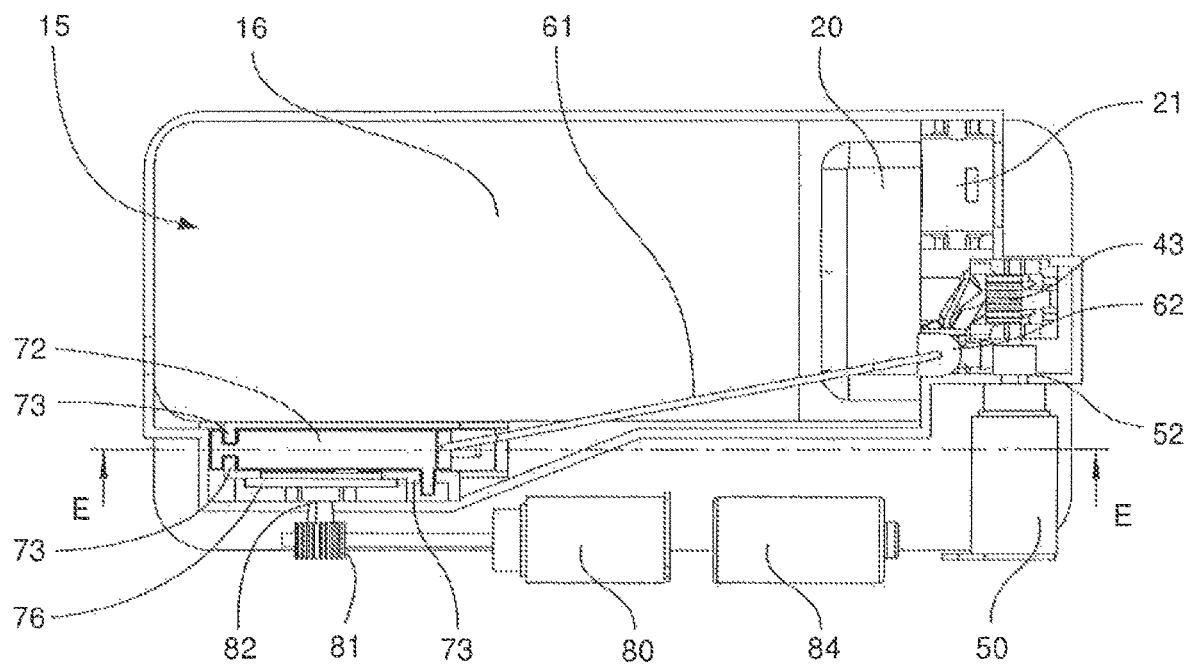
FIG. 5 shows a plan view of the device of FIG. 3 from above in a direction perpendicularly toward a base plate 3.
Figure 6:
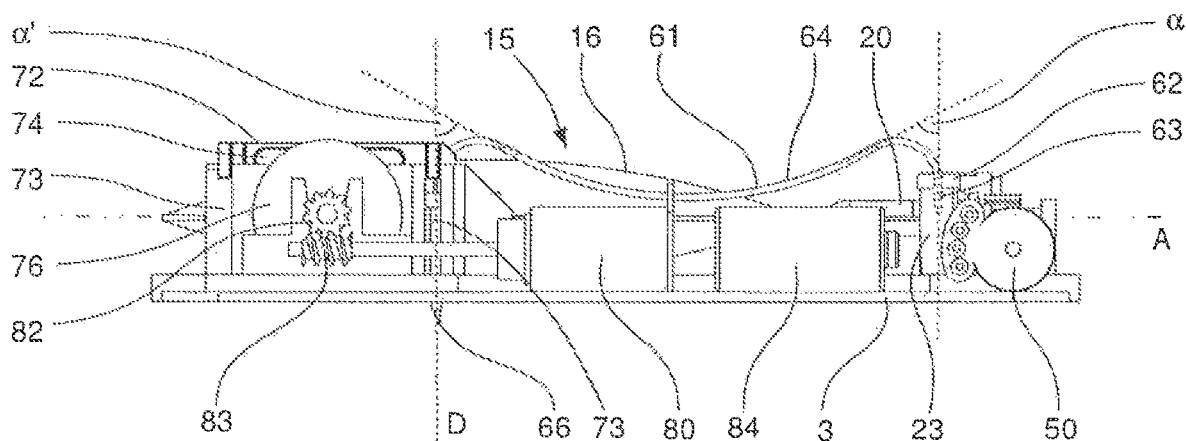
FIG. 6 shows a side view of the device of FIG. 3.
Figure 7:
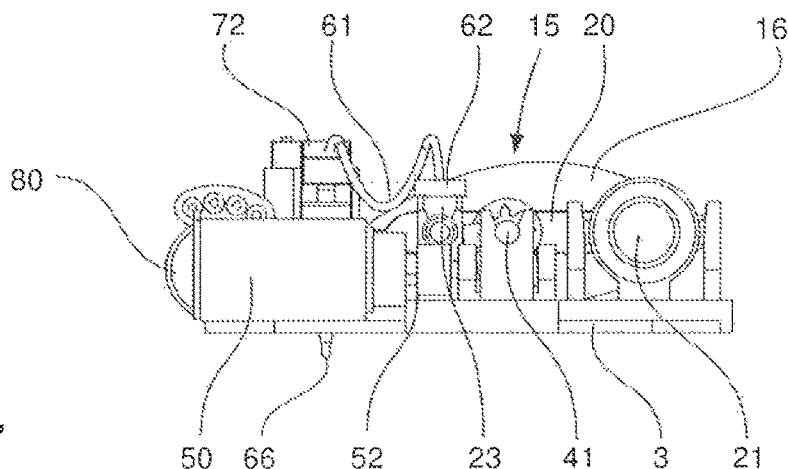
FIG. 7 shows a front view of a face side of the device of FIG. 3 with a filling port.
Figure 8:
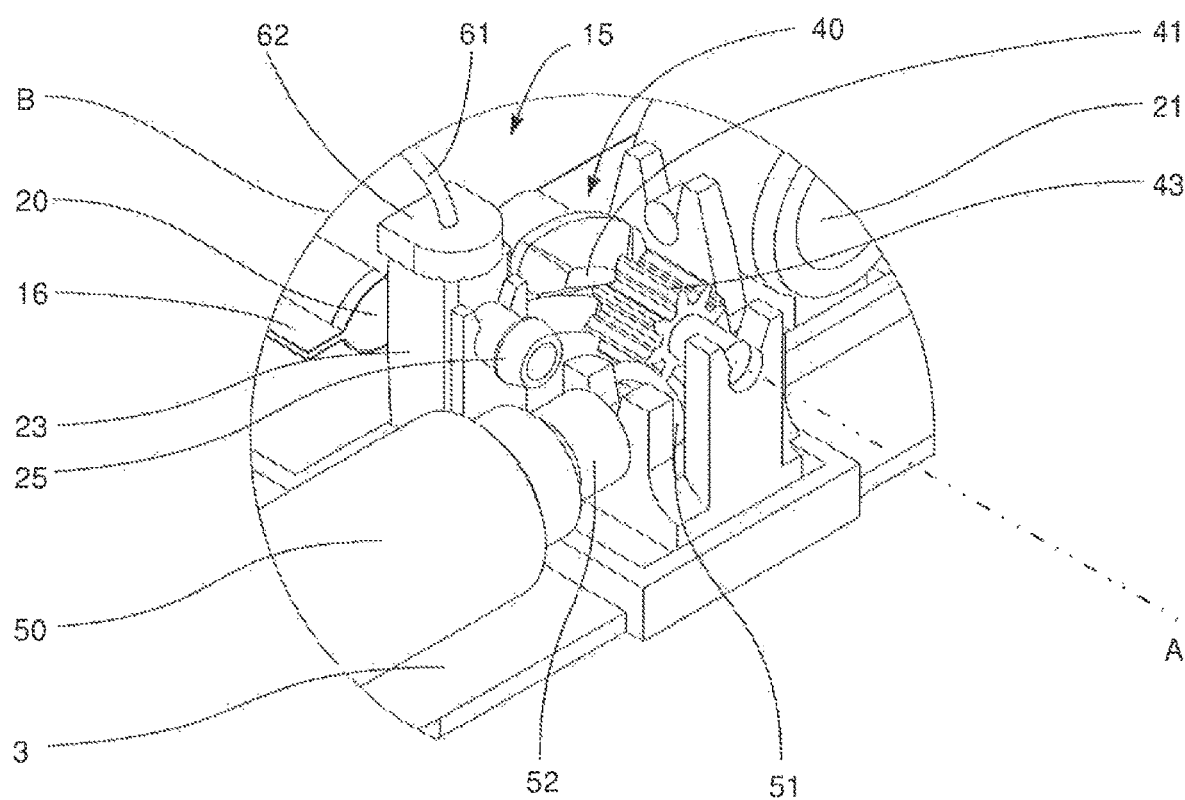
FIG. 8 shows an enlarged detail of a dispensing region as per FIG. 3.
Figure 9:
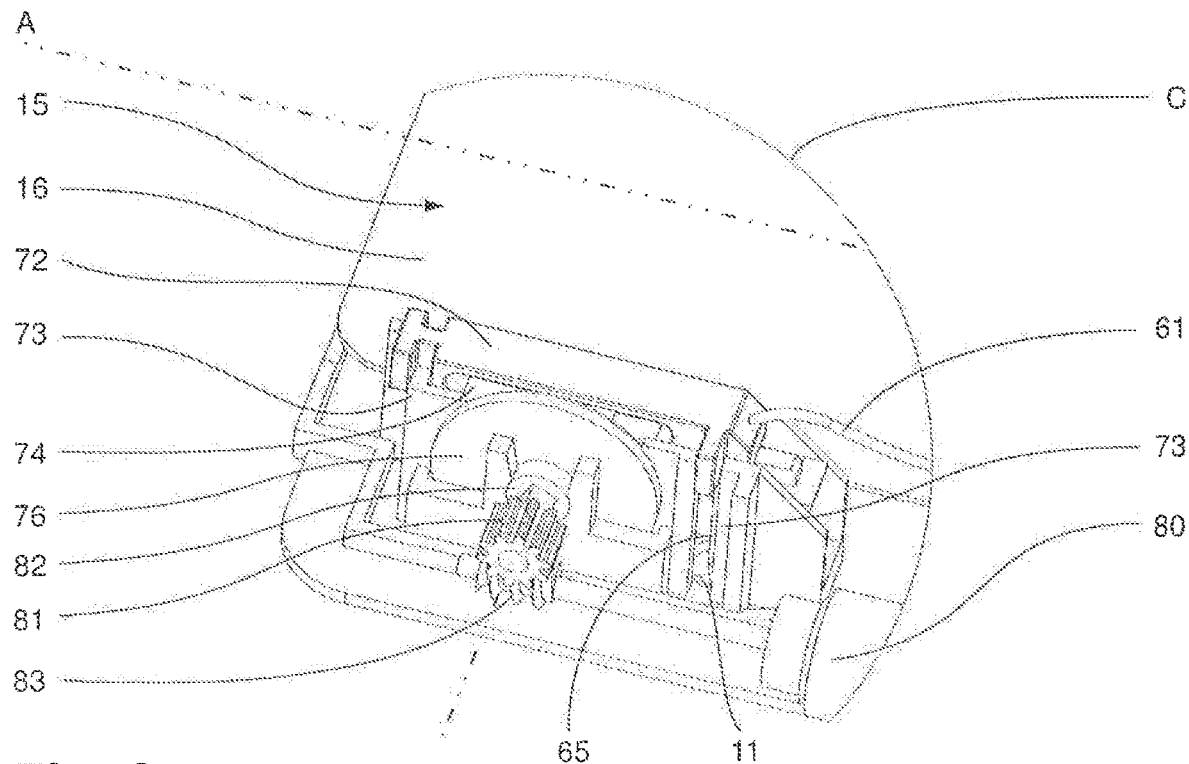
FIG. 9 shows an enlarged detail of an injection region as per FIG. 3.

FIG. 3 shows an oblique view of the device 1 without the housing shells 4 and 5. FIG. 4 shows the drive module 6 on its own without an upper housing part. FIG. 5 shows a plan view of the device 1 from above in a direction perpendicular to the base plate 3 or to the contact surface 10. FIG. 6 shows a side view from the side of the drive, and FIG. 7 shows a front view of the face side with the filling port 21. FIGS. 8 and 9 show enlarged details of a dispensing region B and of an injection region C as per FIG. 3. FIGS. 3 to 9 will be described jointly below.

The container 15 is arranged in the longitudinal direction of A, said container in the present case being of elongate form as a collapsible pouch ("mini bag"), in the interior space 17 of which a fluid is present. Here, the fluid may comprise a medicine, in particular insulin. The container 15 comprises a closure piece 20 which is fixedly connected to a flexible container wall 16. The container wall 16 comprises two layers of a foil material, which are connected to one another in the edge regions at a connecting seam. At one longitudinal end of the container 15, the closure piece 20 is arranged fixedly between the foil layers. Here, the foil layers attach to the closure piece 20 in fluid-tight fashion. The closure piece 20 is described in more detail for example on the basis of FIGS. 15 to 17.

Figure 15:
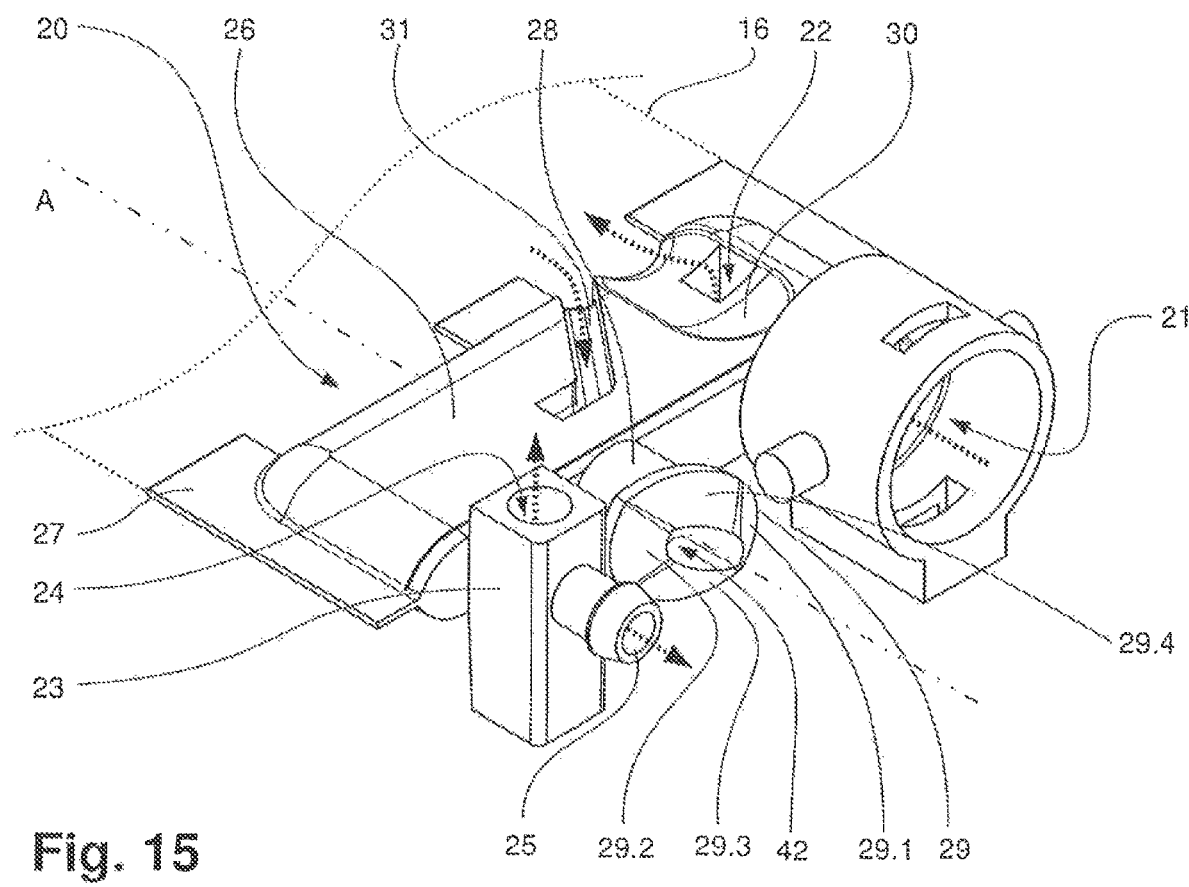
FIG. 15 shows an external oblique view of a closure piece of a container.

Arranged on one face side of a main body 26 of the closure piece 20 is the filling port 21 which communicates via the filling duct 22 with the interior space 17, formed by the foil layers, of the container 15 (see FIG. 15). Via the filling port 21, the interior space of the container 15 can be filled with the fluid as required. On the outer side, the filling port 21 has retention stubs which, for the retention of the container 15 in the device 1, are engaged with detent action into detent brackets of the base plate 3 (see for example FIG. 8).

Likewise formed on the face side on the closure piece 20 is a tubular dispensing port 23 which is oriented perpendicular to the longitudinal direction A and perpendicular to the base plate 3. At an upper tube end, the dispensing port 23 has a dispensing opening 24 (see for example FIG. 15). An opening at a lower tube end of the dispensing port 23 is closed by a closure plug of the base plate 3 (not visible). Furthermore, on the dispensing port 23, there is formed an attachment piece 25 which points forward in the longitudinal direction and which in the present case is closed and to which, for example, a hose can possibly be attached. The attachment piece 25 is furthermore engaged with detent action on a detent bracket of the base plate 3 for the purposes of retaining the container 15 in the device 1 (see for example FIG. 8).

In the dispensing region B (in this regard, see FIG. 8), a delivery device in the form of a wobble piston pump 40 is formed on the closure piece 20 between the filling port 21 and dispensing port 23. The wobble piston pump 40 comprises a piston 41 which projects, with its piston axis, in the direction of A into a stroke chamber 42 of the closure piece 20 (in this regard, see for example FIGS. 18 and 19). In a region which protrudes beyond the closure piece 20, the piston 41 has a gearwheel 43 which is arranged coaxially with respect to the piston axis. At a free end, the piston 41 is mounted on a bearing bracket of the base plate 3, such that the gearwheel 43 is arranged between the closure piece 20 and bearing bracket.

In a direction transverse to the piston axis, a drive axis of a rotary drive 50 is coupled by way of a worm gear 51 to the gearwheel 43 of the piston 41. The worm gear 51 is mounted, so as to be rotatable about an axis of rotation, on bearing brackets of the base plate 3. The axis of rotation is oriented perpendicular to the piston axis. The rotary drive 50 is part of a delivery drive of the wobble piston pump 40. The worm gear 51 and the gearwheel 43 form parts of a drive gearing of the delivery drive.

The rotary drive 50 is coupled by way of its drive shaft to the worm gear 51 by releasable coupling means 52. The coupling means 52 are arranged at in each case one opening in the wall of the housing parts 4 and 5 (not illustrated) and comprise, at the drive shaft side, that is to say on the drive module 6, an axially arranged conical square peg and, at the worm gear side, that is to say on the dispensing module 7, a complementary bushing for the peg. The rotary drive 50 can thus be arranged in the drive module 6, whereas the worm gear 51 is arranged in the dispensing module 7. When the modules 6 and 7 are placed together, the coupling means 52 can be placed in engagement in a predefined engagement direction.

In the embodiments shown, the puncture cannula is formed as one piece as a continuous hollow needle 61.

An attachment nozzle 62 of an injection device 60 is inserted into the dispensing opening 24 of the dispensing port 23. The attachment nozzle 62 is arranged on a hollow needle 61 and produces a fluidic connection between the hollow needle 61 and the dispensing opening 24. A proximal end region 63 of the hollow needle 61, on which the attachment nozzle 62 is arranged, is oriented substantially perpendicular to the base plate 3 and is fixed to the attachment nozzle in the dispensing opening 24 on the dispensing port 23, and thus positionally fixedly in the device 1 (see in particular FIG. 6, for example).

From the proximal end region 63, the hollow needle 61 extends, by way of a central region 64, rearward in the device 1 from the dispensing opening 24 to the injection region C (in this regard, see FIG. 9), with a sight inclination relative to the longitudinal direction A but substantially in the longitudinal direction of A. The injection region C is arranged adjacent to the container 15 in the direction transverse to A. In the injection region C there is formed an application device 70 for the indwelling cannula 67 (see for example FIGS. 10 and 13. The application device 70 comprises a guide device 71 with a runner 72 to which a distal end region 65 (see also for example FIGS. 10 and 11) of the hollow needle 61 is fixedly attached. The distal end region 65 is designed as a puncturing region. The puncturing region 65 is oriented substantially parallel to the proximal end region 63, that is to say likewise substantially perpendicular to the base plate 3. The hollow needle 61 is preferably in the form of a steel cannula.

Here, the central region 64 is arched, that is to say curved, in the direction of the base plate 3, such that the hollow needle 61 is arranged closer to the base plate 3 in the central region 64 than at the dispensing opening 24 or in the injection region C. In other words, the hollow needle 61

"sags" toward the base plate 3 in the central region 64 between the proximal end region 63 and the puncturing region 65.

The runner 72 is mounted on guide rails 73 of the guide device 71 so as to be displaceable in a displacement direction D perpendicular to the base plate 3. The guide rails 73 are fixedly attached to, in particular integrally formed on, the base plate 3. In the illustration of FIGS. 3 to 6, the runner 72 has been displaced away from the base plate 3 to the maximum extent. The puncturing region 65 that is fixedly arranged on the runner 72 has thus been substantially fully retracted into the housing 2 through the application opening 11. A puncturing tip 66 on the distal end of the puncturing region 65 may in this case project outward through the application opening 11 (see for example FIG. 2). If the abovementioned adhesive layer is provided on the contact surface 10, the puncturing tip 66 is protected by the adhesive layer.

An angle α is enclosed between the proximal end region 63 and an adjacent section of the central region 64. The angle α is less than 90 degrees owing to the curvature of the central region 64. Likewise, an angle α' of less than 90 degrees is enclosed between the puncturing region 65 and an adjacent section of the central region 64. Between the proximal end region 63 and the adjacent section of the central region 64, and between the puncturing region 65 and that section of the central region 64 which is adjacent to said puncturing region, the hollow needle 61 is, in a transition region, curved oppositely to the central region 64.

In the runner 72, a guide groove 74 is formed perpendicular to the displacement direction D. The guide groove 74 is engaged into by a cam 75 of a rotary disk 76 of an application gearing, via which an application drive 80 is coupled by way of a drive shaft to the guide device 71. The rotary disk 76 is mounted on bearing brackets of the base plate 3 so as to be rotatable about an axis of rotation perpendicular to the displacement direction D and perpendicular to the longitudinal direction of the guide groove 74. The cam 75 is arranged on the rotary disk 76 eccentrically with respect to the axis of rotation, and engages into the guide groove 74. During a rotation of the rotary disk 76, the runner 74 is, owing to the cam 75, displaced in the guide rails 73 in the displacement direction D.

The rotary disk 76 is coupled by way of coupling means to a gearwheel 81. The gearwheel 81 is in turn coupled by way of a worm gear 83 to the drive shaft of the application drive 80. The drive shaft of the application drive 80 is arranged perpendicular to the axis of rotation of the rotary disk 76, that is to say in particular parallel to the longitudinal direction A. Here, the coupling means 82 are formed analogously to the coupling means 52, wherein the square peg is arranged on the gearwheel and the bushing is arranged on the rotary disk. The coupling means 82 are likewise arranged at a respective opening in the wall of the housing parts 4 and 5. In particular, the engagement directions of the coupling means 52 and 82 are oriented parallel, such that, when the modules 6 and 7 are placed together in the engagement direction, it is simultaneously possible for the application drive 80 to be coupled to the application device 70 and for the rotary drive 50 to be coupled to the wobble piston pump 40.

The application drive 80 is arranged together with the gearwheel 81 and the worm gear 83 in the drive module 6. In the view of FIG. 4, only a base plate 4' of the housing part 4 is illustrated. A bearing arrangement of the gearwheel 81 and of the worm gear 83, and any further bearing and/or fastening means for the retention of the components, are not illustrated in FIG. 4.

The drive module 6 may furthermore comprise an electrical voltage source, such as for example a battery 84, which supplies electrical energy to the application drive 80 and to the rotary drive 50. Furthermore, control electronics (not illustrated) may be provided for controlling the drives 50 and 80, and communication means may be provided, for example for the wireless or wired connection of a remote controller in the drive module 6. Likewise, interfaces may be provided for the exchange of data with an external computer and/or for the supply of electrical energy from an external source. It is self-evidently also possible for monitoring devices to be provided which monitor the drives and the gearings with regard to their correct functioning.

Figure 10:
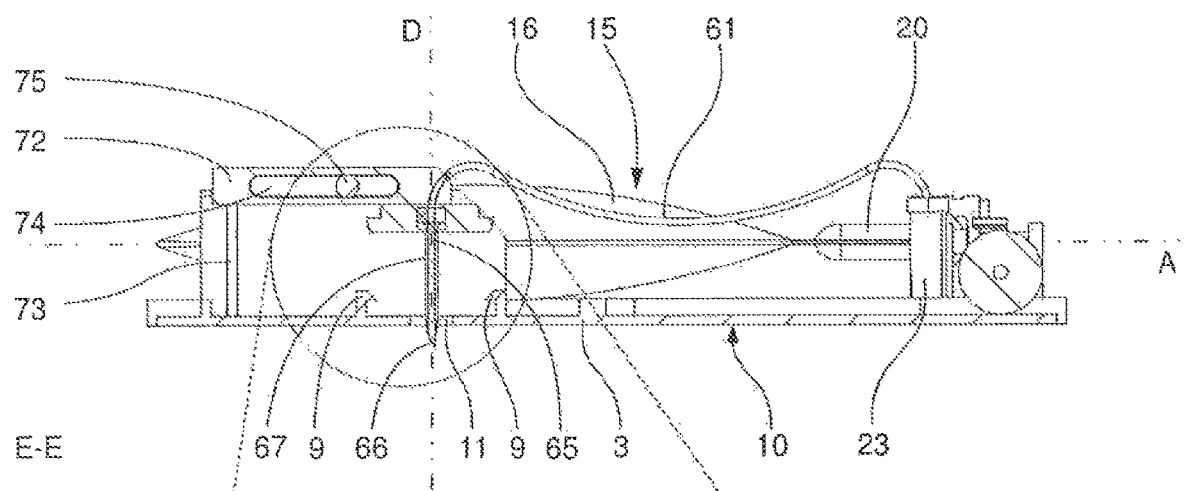
FIG. 10 shows a sectional view in a section plane as per FIG. 5.
Figure 11:
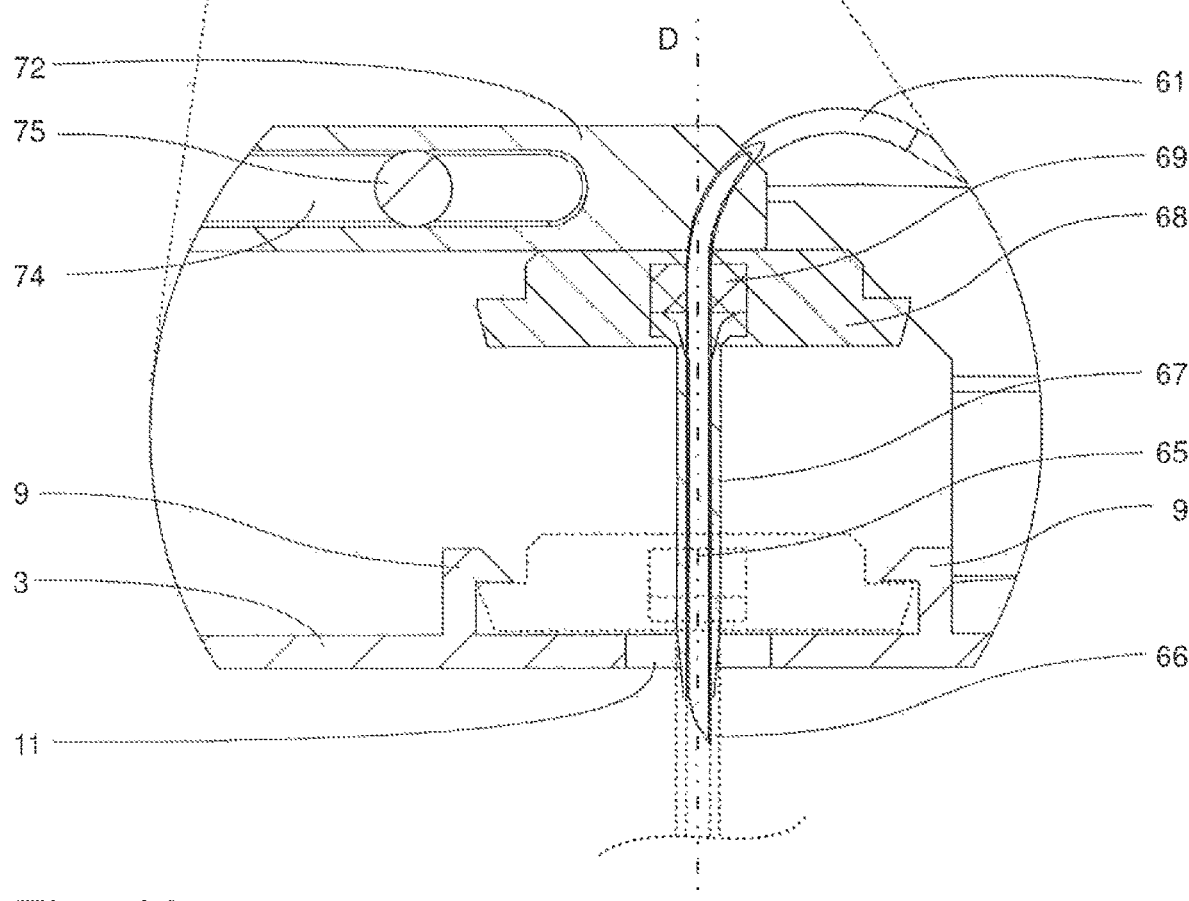
FIG. 11 shows a detail view of the sectional view of FIG. 10 in a puncturing region.

FIG. 10 shows a sectional view in a section plane E (see FIG. 5) which is parallel to A and which encompasses the puncturing direction D, that is to say is oriented perpendicular to the base plate 3. The plane E extends through the puncturing region 65 of the hollow needle 61. FIG. 11 shows a detail view of the sectional view of FIG. 10 in the region of the puncturing region 65. FIGS. 10 and 11 will be described jointly below.

The hollow needle 61 is fastened to the runner 72 in the transition region between the puncturing region 65 and central region 64. Here, the runner 72 may be injection-molded directly around the hollow needle 61 or the hollow needle may be adhesively bonded therein. The puncturing region 65 is oriented in the puncturing direction D and thus perpendicular to the base plate 3. The puncturing tip 66 projects through the application opening 11 slightly. Here, the application opening 11 has an opening area considerably larger than an outer cross section of the indwelling cannula 67. In this way, it is ensured that the indwelling cannula 67 can be deployed through the application opening 11 in contact-free fashion.

The puncturing region 65 is encased by the indwelling cannula 67. Here, the indwelling cannula 67 is manufactured from a flexible biocompatible material which can remain in the body of a patient for a relatively long time. Here, the indwelling cannula 67 is seated sufficiently firmly on the puncturing region 65 that it is driven along by the puncturing region 65 during the movement from the readiness position into the application position during the penetration of the skin of the patient. Here, said indwelling cannula is however seated sufficiently loosely that the indwelling cannula 67 can be pulled off the puncturing region 65 during the retraction of the puncturing region 65 into the end position (in this regard, see also FIGS. 12 to 14).

For this purpose, the base plate 3 comprises a detent means 9 which is arranged at the application opening 11. The indwelling cannula 67 is equipped with a correspondingly complementarily shaped detent means 68 which can be placed in engagement, with detent action, with the detent means 9 when the puncturing region 65 has been deployed together with the indwelling cannula 67 through the application opening 11 into the application position. In the present case, the detent means 9 comprises a detent ring arranged around the application opening 11, and the detent means 68 of the indwelling cannula 67 comprises a detent collar arranged on a proximal longitudinal end of the indwelling cannula 67. The detent collar 68 engages automatically into the detent ring 9 with detent action when the indwelling cannula 67 passes into the application position (indicated by dashed lines in FIG. 11).

Here, the detent collar 68 may be manufactured from a different, for example harder material than the indwelling cannula 67. Typically, the indwelling cannula 67 is fixedly clamped by way of its proximal end section in a passage of the detent collar 68. Furthermore, a sealing element 69 is provided in the passage of the detent collar 68, which sealing element is designed as a sliding seal between the indwelling cannula 67 and the hollow needle 61. The sliding seal 69 ensures that, in all relative positions of the hollow needle 61 and indwelling cannula 67, a fluid-tight connection exists between the hollow needle 61 and the indwelling cannula 67.

Here, in the readiness position, the detent collar 68 preferably beats against the runner 72 of the guide device 71, such that an exertion of force by the runner 72 during the puncturing movement also acts directly on the detent collar 68 and on the indwelling cannula 67. Furthermore, when the application position is reached, the detent collar 68 is reliably pressed into the detent ring 9 by the runner 72.

Figure 12:
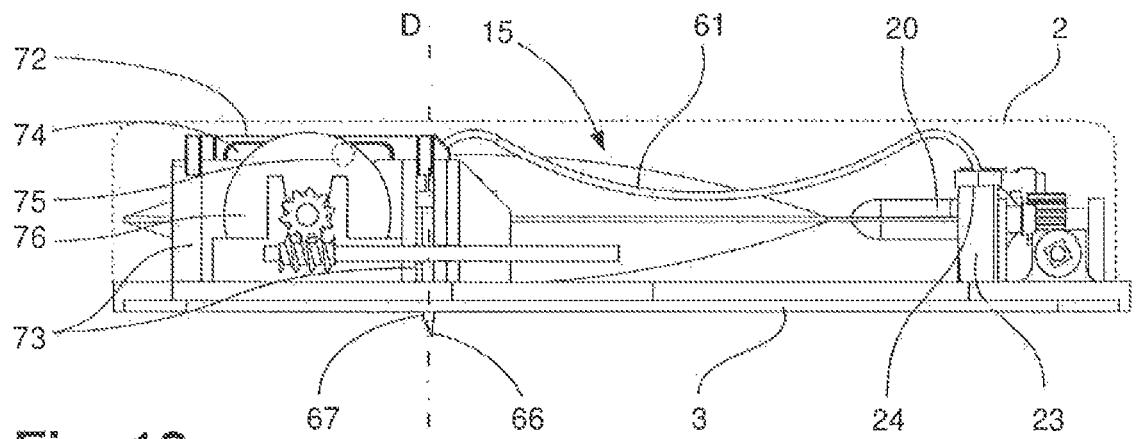
FIG. 12 shows a side view of the device as per the illustration of FIG. 6, with the application drive having been omitted and with an injection device in the readiness position.
Figure 13:
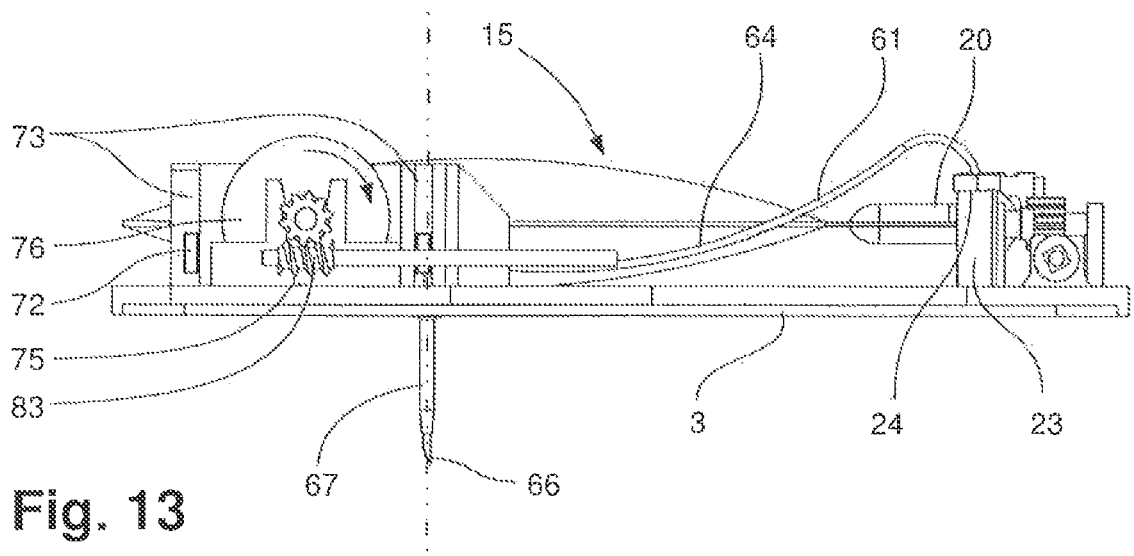
FIG. 13 shows a side view as per FIG. 12 with the injection device in the application position.
Figure 14:
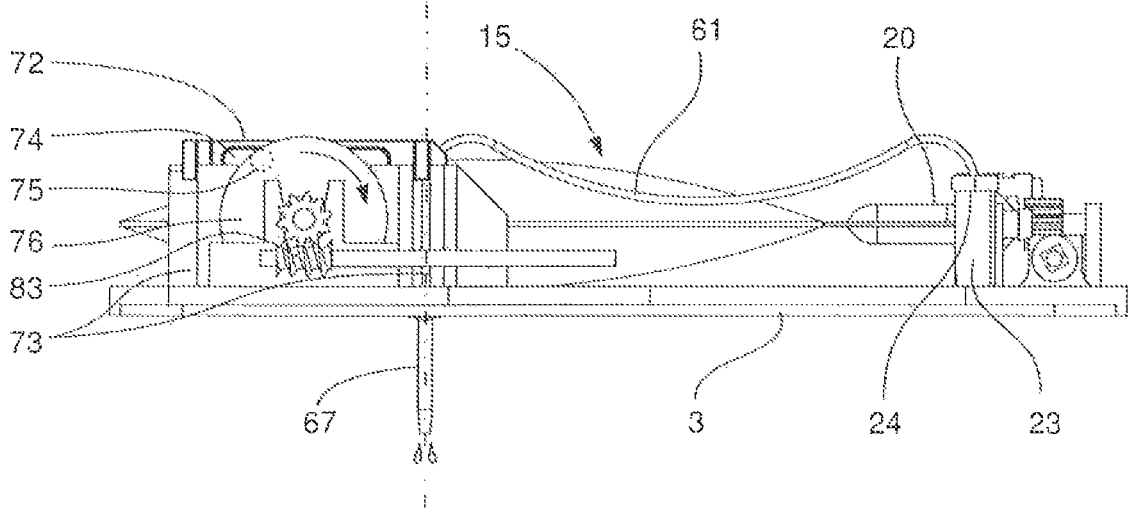
FIG. 14 shows a side view as per FIG. 12 with the injection device in the end position.

FIGS. 12 to 14 show side views of the device 1 substantially corresponding to FIG. 6, wherein FIG. 12 shows the injection device 60 in the readiness position, FIG. 13 shows said injection device in the application position, and FIG. 14 shows said injection device in the end position.

FIG. 12 corresponds substantially to the illustration of FIG. 6, wherein the application drive 80 and the battery 84 and the rotary drive 50 have been omitted for better clarity. The runner 72 has been displaced in the guide rails 73 away from the base plate 3 to the greatest possible extent. The puncturing region 65 of the hollow needle 61 is arranged substantially entirely in the housing 2 (not illustrated). The puncturing tip projects through the application opening 11 and slightly beyond the contact surface 10.

In FIG. 13, the runner 72 has been displaced toward the base plate 3 to the full extent. The displacement is effected by rotation of the rotary disk 76 in an application direction (see arrow), whereby the cam 75 arranged on said rotary disk is lowered toward the base plate 3. Here, the cam 75 drives the runner 72 along while being displaced in the longitudinal guide 74 transversely with respect to the puncturing direction or the displacement direction D of the guide device 71.

With the displacement of the runner 72, the puncturing region 65, which is fixedly attached thereto, of the hollow needle 61 is deployed through the application opening 11. The indwelling cannula 67 is thereby moved into the application position, wherein the detent collar 68 engages with detent action in the detent ring (not visible). Owing to the linear displacement of the runner 72, the distance to the dispensing opening 24, which is arranged fixedly in the housing 2, is greater than that in the readiness position. The length compensation of the hollow needle 61 that is thus required is achieved by way of the central region 64 of the hollow needle 61, which in the application position is stretched, that is to say has a reduced curvature, in relation to the readiness position. Owing to the guide device 71, the hollow needle 61 can have a relatively high stiffness and may for example be manufactured from steel, without the puncturing movement being disrupted by the force that is required to effect the stretching. The guide device 71 ensures that the puncturing region 65 penetrates the skin of the patient rectilinearly.

FIG. 14 shows the injection device 60 in the end position. Further rotation of the rotary disk 76 in the application direction has the effect that the runner 72 is, by way of the cam 75, displaced back again, away from the base plate 3. The position of the runner 72 in the end position corresponds to the position in the readiness position. Here, the puncturing region 65, which is fixedly connected to the runner 72, of the hollow needle 61 is also retracted through the application opening 11 into the housing 2. Here, the indwelling cannula 67, which is engaged with detent action by way of the detent collar 68 in the detent ring 9 of the base plate, remains in the application position. The indwelling cannula 67 is thus at least partially pulled off the puncturing region 65. In the end position, an end region at the puncturing tip 66 of the puncturing region 65 projects into the indwelling cannula 67 (not visible). In particular, the sealing element 69 bears in fluid-tight fashion against the outside of the end region of the puncturing tip 66. In this way, fluid from the container 15 can be fed to the applied indwelling cannula 67 from the dispensing opening 24 via the hollow needle 61.

Owing to the worm gear 83, the rotary disk 76, once it has assumed a rotary position, is fixed in said position in each case. By way of the cam 75, the runner 72 is thus also fixed, such that an inadvertent redeployment or puncturing movement of the hollow needle 61 is reliably prevented. The worm gear 83 thus forms, together with the rotary disk 76, a part of a self-locking application gearing of the application device 70.

Figure 16:
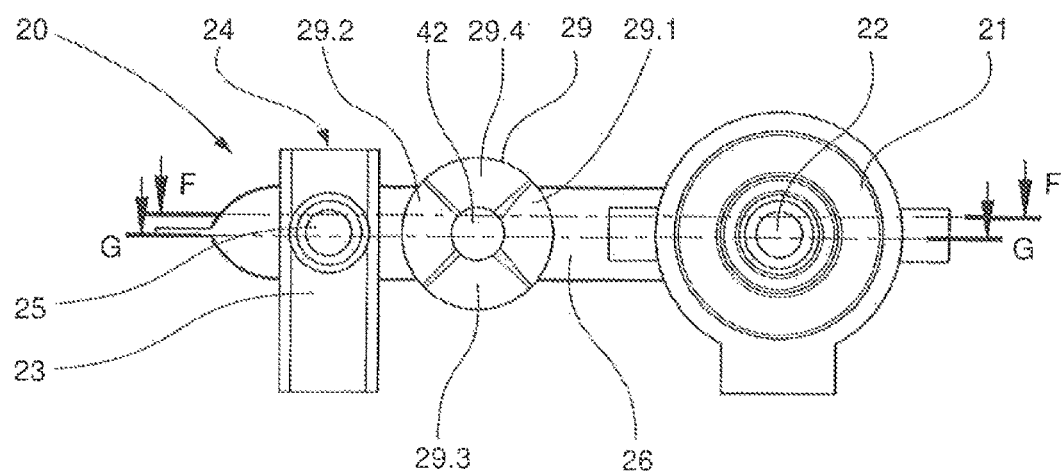
FIG. 16 shows a view of a face side of the closure piece.
Figure 17:
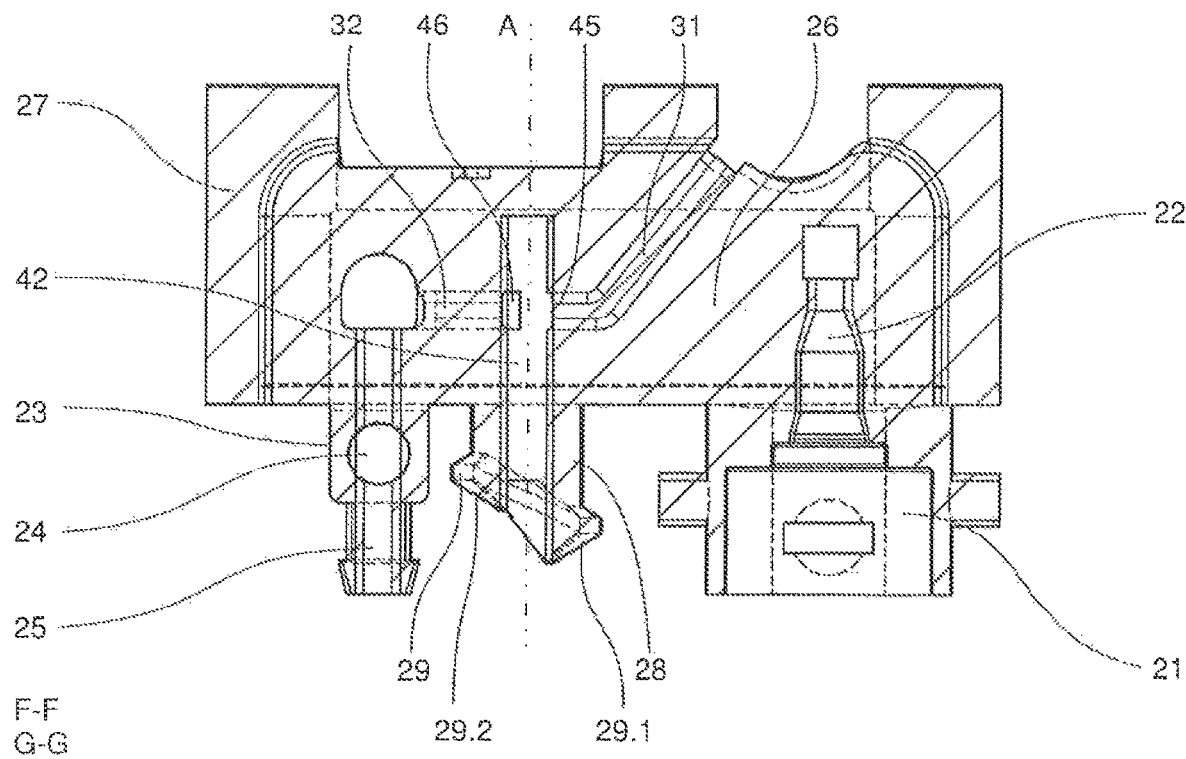
FIG. 17 shows a doubly sectional view of the section planes indicated in FIG. 16.

FIG. 15 shows an external oblique view of the closure piece 20. FIG. 16 shows a view, along A, of the face side of the closure piece 20, and FIG. 17 shows a doubly sectional view as per the section planes F and G shown in FIG. 16. FIGS. 15 to 17 will be described jointly below.

The closure piece 20 is in the present case in the form of a unipartite injection-molded part. The main body 26 has a cross section which is flattened in a direction perpendicular to A and which, toward the edges, ends in a flange 27 extending around part of the periphery. Here, the flange 27 serves for joining together the foil layers which form the container wall 16 and between which the closure piece 20 is arranged. The closure piece 20 comprises a connector 28 which extends forward in the direction of A from the face side of the closure piece 20. The stroke chamber 42 of the wobble piston pomp 40 is in the form of a forwardly open, circular cylindrical hollow chamber in the connector 28 and extends into the main body 26. The stroke chamber 42 is in the present case formed coaxially with respect to A.

A face side of the connector 28 is of beveled form with respect to A and has a flange 29 which projects substantially radially outward with respect to A. The flange 29 is formed as a control surface for the piston 41 (in this regard, see for example FIG. 17). The control surface 29 has, at the circumference, a varying spacing in the direction of A from the face side of the closure piece 20, such that a runner 44 (see for example FIGS. 18 and 19), which is guided on the control surface 29, of the piston 41 forcibly imparts a stroke movement to the piston 41 when the latter is rotated about A. Depending on the design of, for example, the piston 41 and the stroke chamber 42, the control surface 29 may have sections of different gradient, such that a stroke that can be generated as a result of a rotation may vary depending on the rotational position of the piston 41. In the present case, the control surface 29 comprises four sections, of which two sections 29.1 and 29.2, which are situated opposite one another with respect to A, are of perpendicular form in different longitudinal positions with respect to A, and the two further sections 29.3 and 29.4 are inclined with respect to A and adjoin the sections 29.1 and 29.2.

In the main body 26 there is formed the filling duct 22 which communicates with the interior space 17 of the container 15. Here, the filling duct 22 emerges at the face side at the filling port 21. The filling port 21 has a circular cylindrical tube section as a coupling element for coupling to a fluid source. On an underside of the tube section there is formed a support surface by which the filling port 21 can be supported on and possibly fastened to the base plate 3 of the housing 2.

Toward the interior space of the container 15, the filling duct 22 opens out at a depression 30, which is formed in the main body 26, of the closure piece 20. The depression 30 ensures that a fluid can enter the interior space 17 through the fluid duct 22. At the same time, the depression 30 forms a support surface against which one of the foil layers of the container wall 16, which foil layer covers the depression 30, can be pressed from the outside in order to close off the filling duct 22 in fluid-tight fashion. For this purpose, an internal projection may be formed for example on the housing 2 (not illustrated), which projection is designed and dimensioned such that, in the operationally ready state, the foil layer presses the foil sealingly into the depression 30. Alternatively, in the filling duct 22, there may be formed a duckbill valve (not illustrated) which prevents a return flow of the fluid out of the interior space 17 through the filling duct 22.

Furthermore, an extraction duct 31 is formed in the main body 26, which extraction duct likewise communicates with the interior space of the container 15. The extraction duct 31 issues, directly adjacent to the depression 30, into the interior space 17 of the container 15 and is covered by the same foil layer as the depression 30. The extraction duct 31 extends toward the stroke chamber 42 and issues into the stroke chamber 42 at a supply opening 45 which is elongate in the direction A (see for example FIG. 17).

At a discharge opening 46 (see for example FIG. 17) a dispensing duct 32 which extends in the interior of the main body 26 issues into the stroke chamber 42. The supply opening 45 and discharge opening 46 are, with respect to the stroke chamber axis, that is to say in the present case with respect to the longitudinal axis A, arranged substantially oppositely on a shell-side inner wall of the stroke chamber 42.

The dispensing duct 32 extends to the tubular dispensing port 23 which is formed on the face side of the closure piece 20. The dispensing duct 32 communicates with an interior space of the dispensing port and with the dispensing opening 24 and attachment opening 25 formed thereon.

Figure 18:
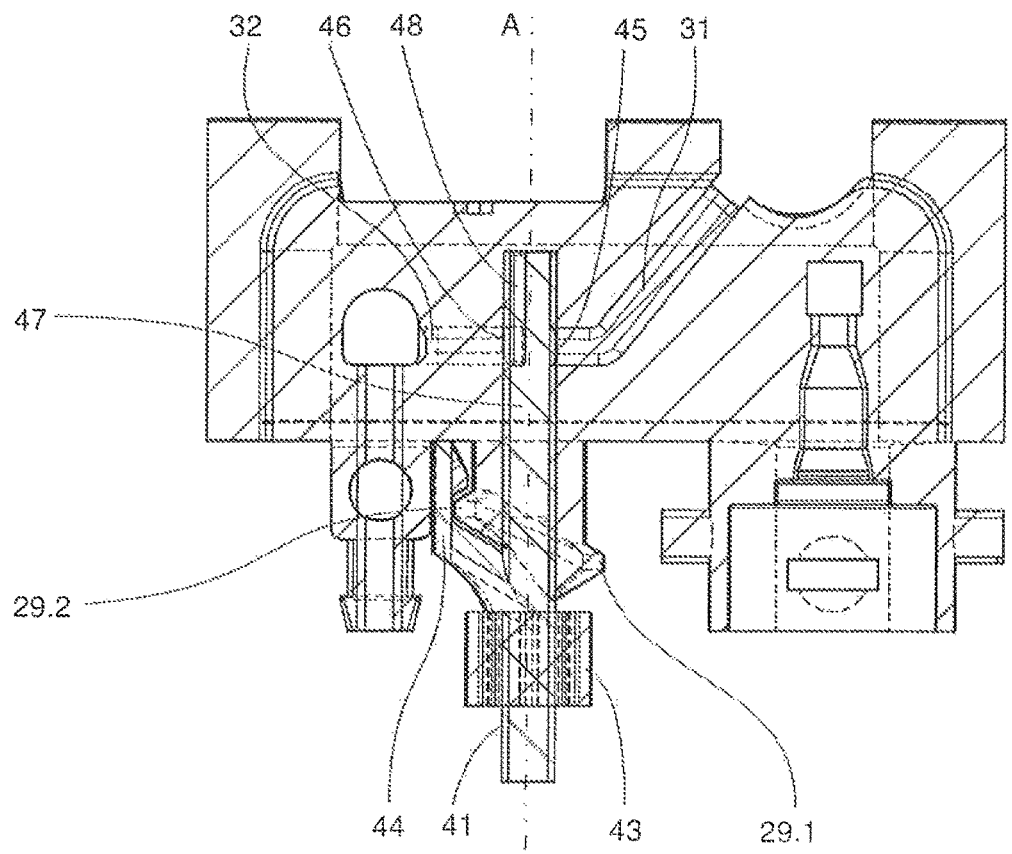
FIG. 18 shows a doubly sectional view as per FIG. 17 with a piston of a delivery device, said piston having been retracted fully into a stroke chamber in the closure piece.
Figure 19:
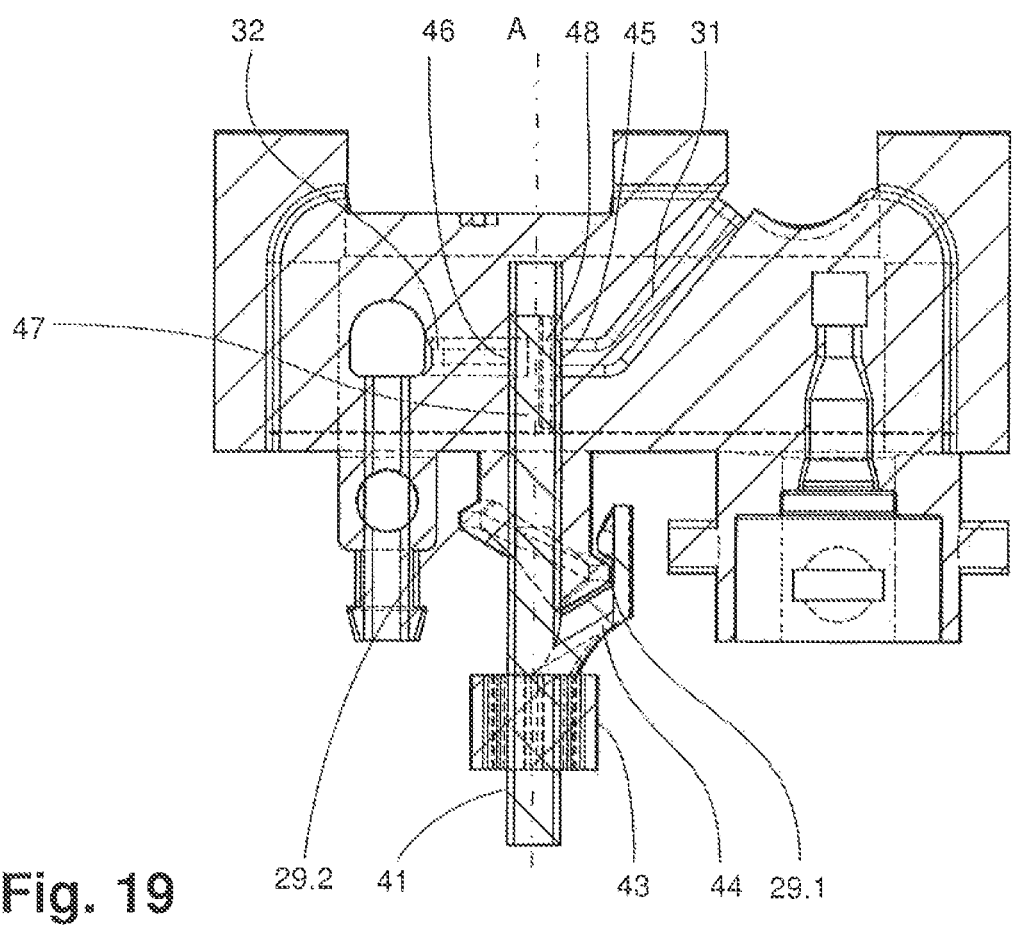
FIG. 19 shows a doubly sectional view analogous to FIG. 18 with the piston fully deployed.

FIGS. 18 and 19 show doubly sectional views, analogous to FIG. 17, of the closure piece 20 with piston 41 arranged thereon. In FIG. 18, the piston 41 has been fully retracted into the stroke chamber 42, and in FIG. 19, the piston has been fully deployed.

The piston 41 has a substantially circular cylindrical main body 47, the outer dimensions of which correspond, with a mobility tolerance, to the inner dimensions of the stroke chamber 42. The gearwheel 43 is formed on a section which projects out of the stroke chamber 42. Arranged on the main body 47 is the runner 44 which engages around the control surface 29 on both sides in the direction of A. Positive coupling between the rotational movement and the stroke movement of the piston 41 is achieved in this way.

A longitudinal channel 48 is arranged on the shell of that end section of the piston which is arranged in the stroke chamber 42. The longitudinal channel 28 is in this case in fluid communication, depending on the rotational position of the piston 41, with the supply opening 45, with the discharge opening 46, or with neither of the two openings. Thus, a distinction can be made between substantially four pump strokes, which correspond to the four sections 29.1 to 29.4 of the control surface 29:

On the rising or falling sections 29.3 and 29.4, the longitudinal channel 48 is in fluid communication either with the discharge opening 46 or with the supply opening 45. Owing to the stroke movement, the piston 41 acts either as a displacement body, which displaces a fluid in the stroke chamber 42 through the discharge opening 46 into the dispensing duct 32, or as a suction piston, which draws the fluid through the extraction duct 31 into the stroke chamber 42. In the sections 29.1 and 29.2, the piston 41 does not perform a stroke movement, such that the volume in the stroke chamber 42, which volume is defined by the piston 41, remains constant. In the strokes defined by the sections 29.1 and 29.2, the longitudinal channel 48 is rotated from the supply opening 45 to the discharge opening 46 or vice versa.

In FIG. 18, the runner 44 is situated on the section 29.2 of the control surface 29, and in FIG. 19, said runner is situated on the section 29.1, which is situated further remote, in the direction A, from the main body 26 of the closure piece 20.

FIGS. 20 to 23 show the four working strokes of the wobble piston pump 40, in each case in an external oblique view and in a transparent view.

FIG. 20 shows the first stroke during the movement of the runner 44 from the section 29.2 onto the rising section 29.4. At this point, the piston 41 is still fully retracted in the stroke chamber 42. Here, the longitudinal channel 48 is in fluid communication with the supply opening 45.

FIG. 21 shows the second stroke, during which the piston 41 is forced out of the stroke chamber 42 by the section 29.4. Here, owing to the negative pressure thus generated in the stroke chamber 42, the fluid is drawn into the stroke chamber 42 via the extraction duct 31 by the piston 41.

FIG. 22 shows the third stroke during the movement of the rotor 44 from the section 29.1 to the falling section 29.3. At this point, the piston 41 is still fully deployed out of the stroke chamber 42. Here, the longitudinal channel 48 is in fluid communication with the discharge opening 46.

Finally, FIG. 23 shows the fourth and final stroke, during which the piston 41 is forced into the stroke chamber 42 by the section 29.3. Here, owing to the positive pressure that is thus generated in the stroke chamber 42, the fluid is forced out of the stroke chamber 42 via the dispensing duct 32 by the piston 41.

After the fourth stroke, the working cycle of the wobble piston pump 40 begins again from the start with the first stroke.

Figure 24:
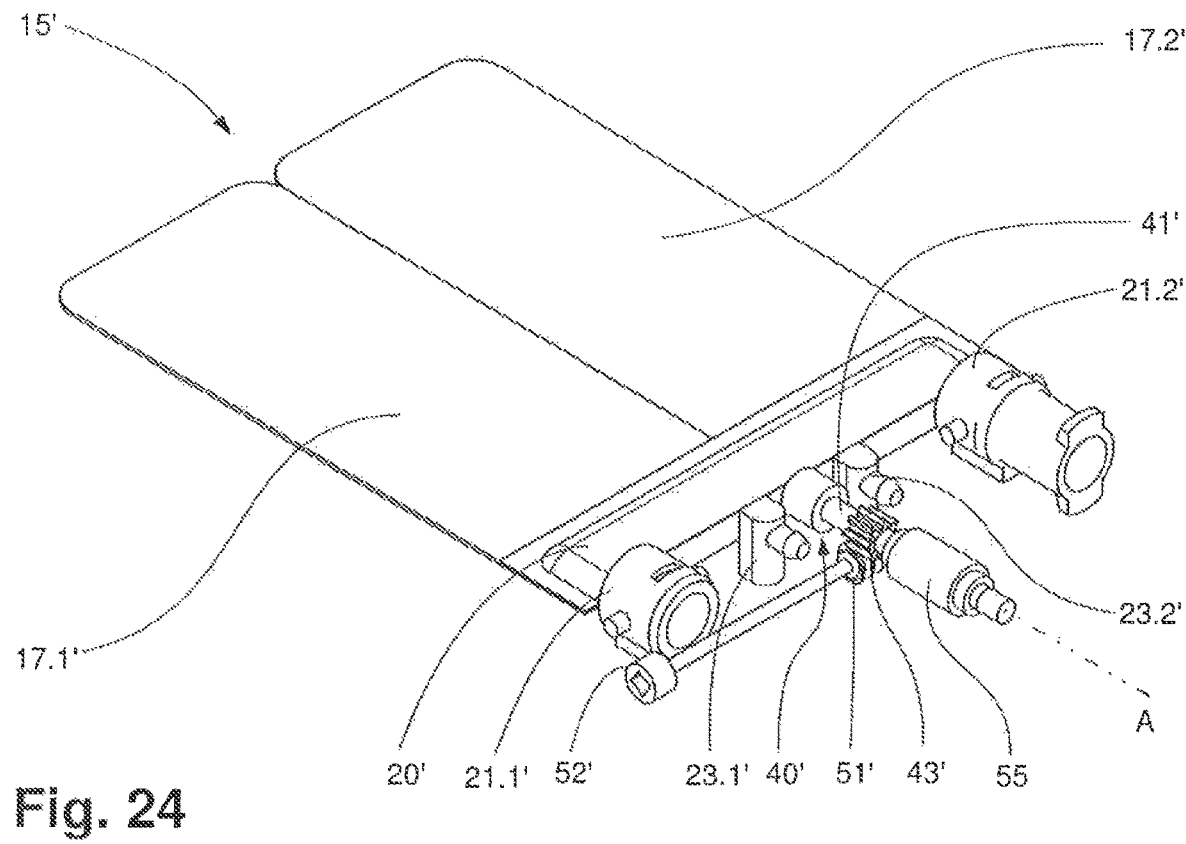
FIG. 24 shows an external oblique view of a container of a device according to the invention with multiple interior spaces.
Figure 25:
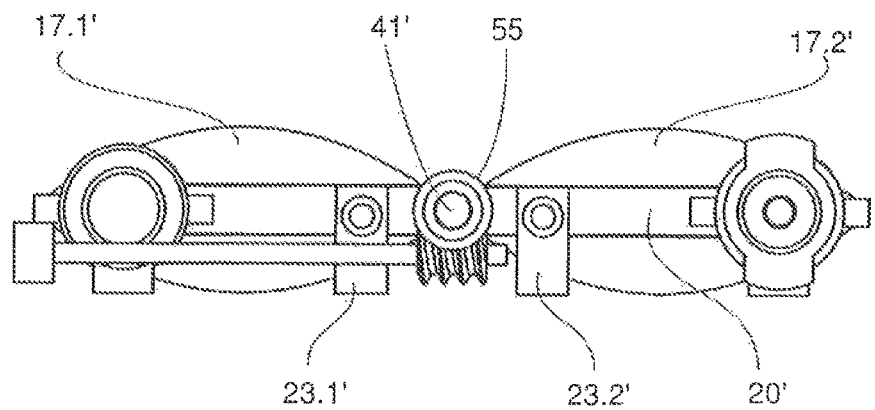
FIG. 25 shows a front view of a face side of the container of FIG. 24.
Figure 26:
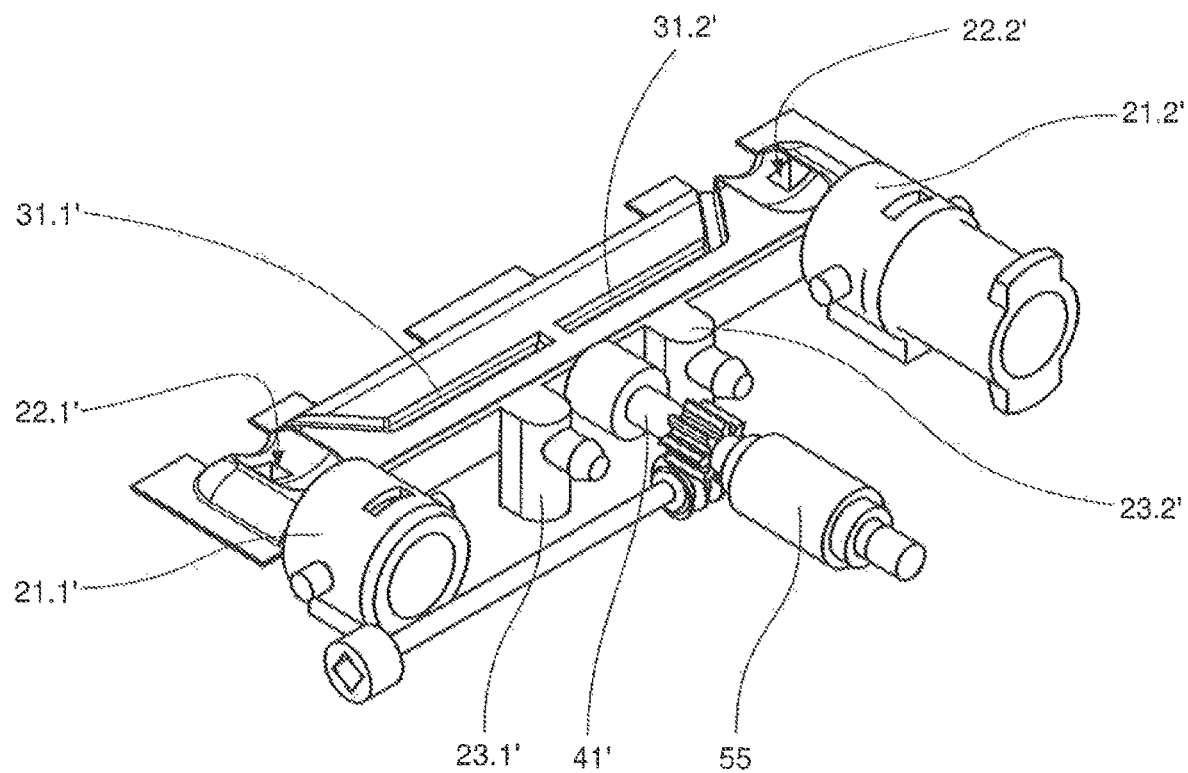
FIG. 26 shows an external oblique view of a closure piece of the container as per FIG. 24 from above.
Figure 27:
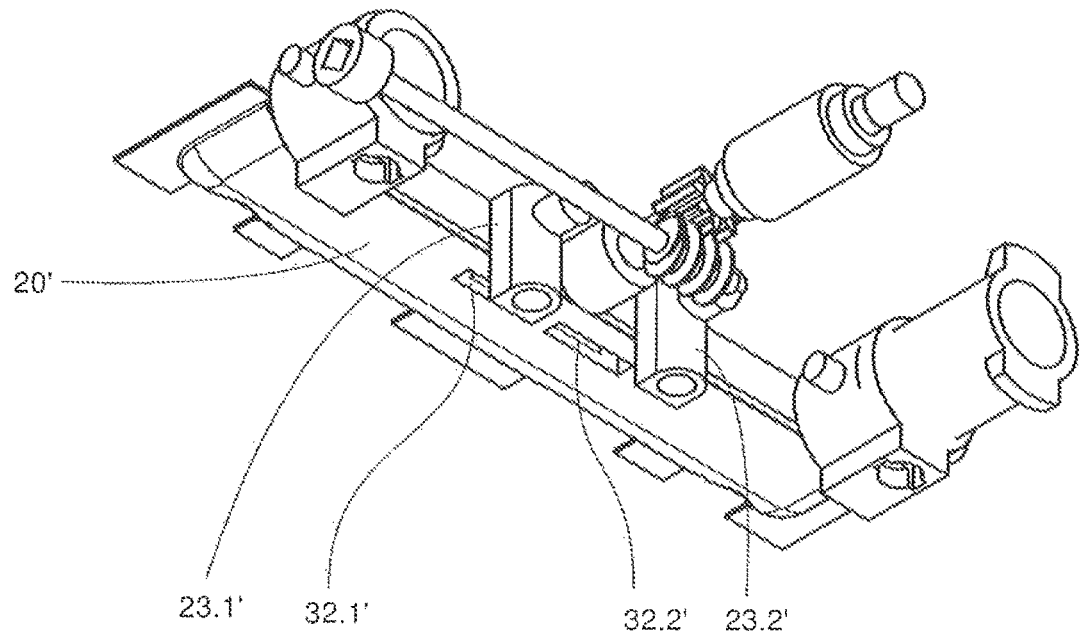
FIG. 27 shows an external oblique view of a closure piece of the container as per FIG. 24 from below.

FIGS. 24 and 25 show views of a container 15' with multiple interior spaces 17.1' and 17.2' of a further embodiment of a device according to the invention. Housing parts and the injection device of the device are not illustrated, and may be designed, with slight modifications, as per the preceding figures. FIGS. 26 and 27 show external oblique views of the closure piece 20' from above and below. FIGS. 24 to 27 will be described jointly below.

The interior spaces 17.1' and 17.2' are delimited with respect to one another in fluid-tight fashion. The two interior spaces 17.1' and 17.2' are provided by way of an additional connecting seam of the foil layers in the direction of A. The container 15' has a single closure piece 20' to which both interior spaces 17.1' and 17.2' are attached. The closure piece 20' has two filling ports 21.1' and 21.2' which are assigned to in each case one of the interior spaces 17.1' and 17.2' and which communicate with these via filling ducts 22.1' and 22.2'.

On the closure piece 20' there is formed a central wobble piston pump 40' with a piston 41'. The piston 41' projects, from the outside, into a stroke chamber of the closure piece 20'. To an outwardly projecting section of the piston 41' there is coupled a linear drive 55 which, as a stroke drive, drives a stroke movement of the piston 41'. A rotational movement of the piston 41' is, analogously to the situation in the device 1, realized by way of a drive gearing comprising a worm gear 51' which engages into a gearwheel 43' of the piston 41'. The worm gear 51' can be coupled by way of a coupling means 52' to a rotary drive (not illustrated). Owing to the separate stroke drive 55, the control surface 29 and the runner 44 of the piston, such as are provided for example in the case of the device 1, are omitted.

On the closure piece 20' there are formed two dispensing ports 23.1' and 23.2' which are formed substantially analogously to the dispensing port 23 of the device 1. The dispensing ports 23.1' and 23.2' are each in fluid communication with dispensing ducts 32.2' and 32.2'. The dispensing ducts 32.1' and 32.2' issue into the stroke chamber at in each case one discharge opening (not illustrated).

Furthermore, on the closure piece 20', there are formed two extraction ducts 31.1' and 31.2' which issue into in each case one of the interior spaces 17.1' and 17.2'. The extraction ducts 31.1' and 31.2' furthermore issue into the stroke chamber at in each case one supply opening (not illustrated). Here, the supply openings and the discharge openings are arranged on the shell of the inner wall of the stroke chamber with the same axial spacing. The stroke chamber can thus, by way of a longitudinal channel of the piston 41', be placed in fluid communication selectively with in each case one of the openings in a manner dependent on the rotational position. The central wobble piston pump 40' thus permits a selective extraction of fluids from the interior spaces 17.1' and 17.2' and a selective feed to the dispensing ports 23.1' and 23.2'.

Figure 28:
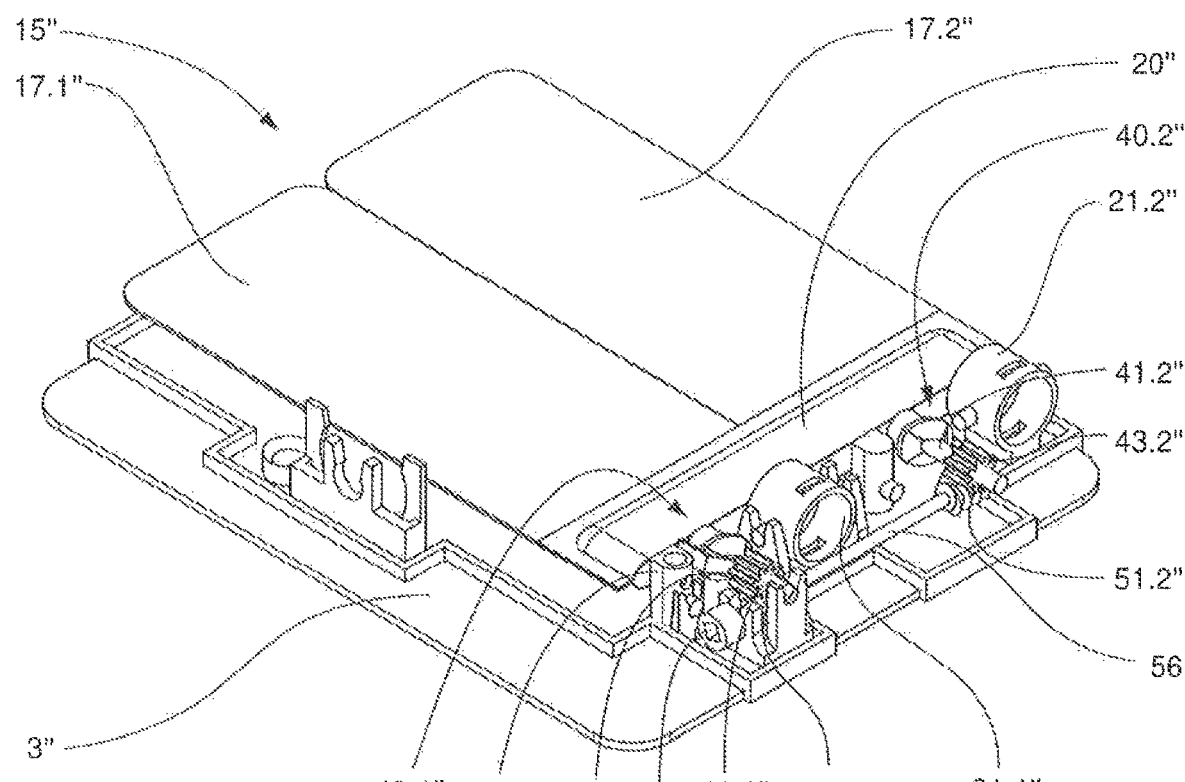
FIG. 28 shows an external oblique view of a further container of a device according to the invention with multiple interior spaces and multiple delivery devices.
Figures 29, 30:
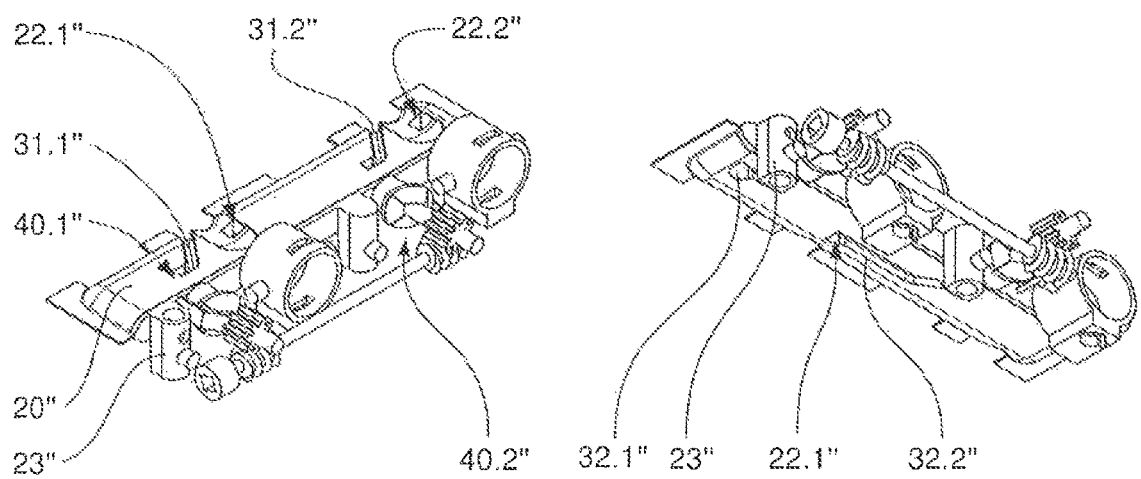
FIG. 29 shows an external oblique view of the closure piece of the container as per FIG. 28 from above.
FIG. 30 shows an external oblique view of the closure piece of the container as per FIG. 28 from below.
Figure 31:
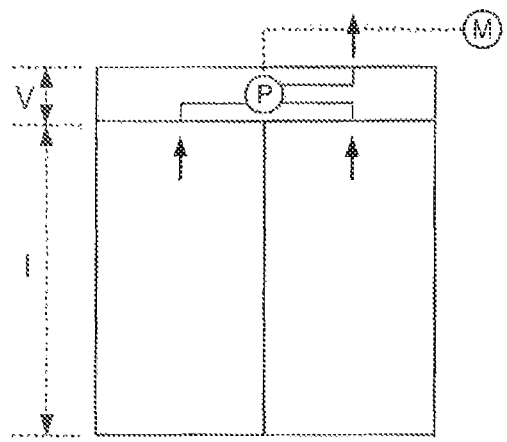
FIGS. 31-35 show various function diagrams showing the manner in which the interior spaces of a double-chamber container can be fluidically connected to one or two pumps.
Figure 32:
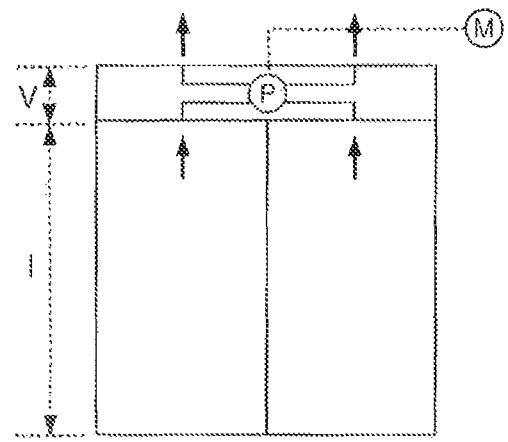
Figure 33:
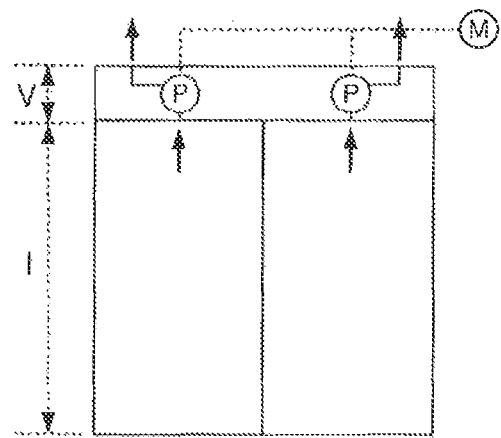
Figure 34:
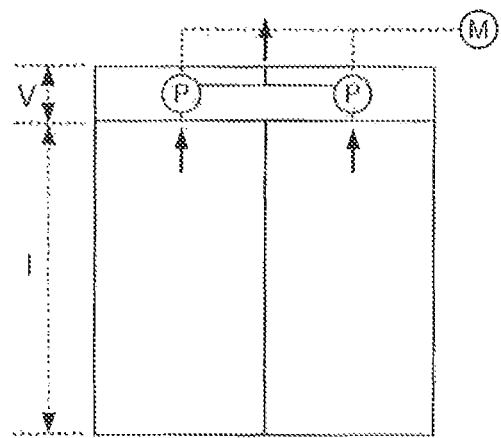
Figure 35:
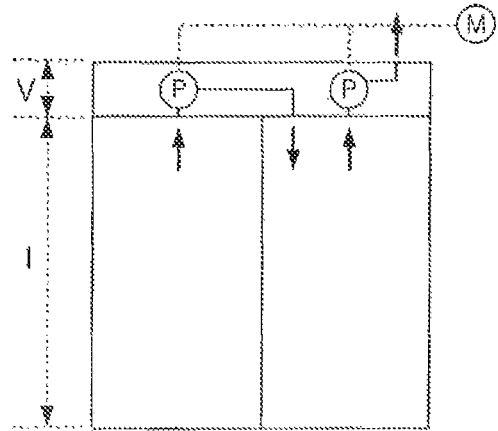

FIG. 28 shows an oblique view of a further container 15" with multiple interior spaces 17.1" and 17.2" of a further embodiment of a device according to the invention, which is arranged on a base plate 3" of a housing of the device. The container 15" has a single closure piece 20" to which the two interior spaces 17.1" and 17.2" are attached. The closure piece 20" has two filling ports 21.1" and 21.2", which are assigned to in each case one of the interior spaces 17.1" and 17.2" and which communicate with these via filling ducts 22.1" and 22.2". FIGS. 29 and 30 show oblique views of the closure piece 20" from above and from below. FIGS. 28 to 30 will be described jointly below.

On the closure piece 20" there are formed two wobble piston pumps 40.1" and 40.2" with in each case one piston 41.1" and 41.2". The pistons 41.1" and 41.2" project in each case from the outside into a stroke camber (not visible) of the closure piece 20". A single rotary drive can be coupled, by way of a coupling rod 56, to an outwardly projecting section of the pistons 41.1" and 41.2". The coupling rod 56 has two worm gears 51.1" and 51.2" which are coupled by way of in each case one gearwheel 43.1" and 43.2" to the pistons 41.1" and 41.2". On the coupling rod 56 there is formed a coupling means 52" by which a rotary drive can be coupled on. In this way, both wobble piston pumps 40.1" and 40.2" can be driven by way of only one rotary drive. The stroke movement is generated, analogously to the situation in the device 1, by way of control surfaces of the closure piece 20".

The stroke chambers of the two wobble piston pumps 40.1" and 40.2" communicate in each case via an extraction duct 31.1" and 31.2" with a respective one of the interior spaces 17.1" and 17.2". A dispensing duct 32.2" which adjoins the stroke chamber of the wobble piston pump 40.2" issues into the interior space 17.1". A dispensing duct 32.1" communicates with a dispensing port 23" which is of substantially analogous design to the dispensing port 23 of the device 1.

The wobble piston pump 40.2" thus delivers a fluid from the interior space 17.2" into the interior space 17.1", whereas the wobble piston pump 40.1", owing to the coupling by way of the piston rod 56, simultaneously delivers a fluid from the interior space 17.1" to the dispensing port 23". In this way, it is for example possible for two separately stored fluids to be mixed before being dispense, or it is possible for a solid medicine to be provided in the interior space 17.1", which solid medicine can, before being dispensed, be dissolved in the fluid of the second interior space 17.2". It is self-evidently also possible in this case for the stroke movement of the two pumps to be decoupled, and to be generated for example by way of separate stroke drives, analogously to the embodiment of FIGS. 24 to 27.

FIGS. 31 to 35 show various function diagrams showing the manner in which the interior spaces of a double-chamber container can be fluidically connected to one or two pumps P. M denotes a pump drive, V denotes the regions of the closure piece, and I denotes the regions of the interior spaces. Here, the diagram of FIG. 32 corresponds to the embodiment of FIGS. 24 to 27, and the diagram of FIG. 35 corresponds to the embodiment of FIGS. 28 to 30. It is readily apparent how the corresponding arrangements can also be extended to containers having more than two interior spaces.

Figure 36:
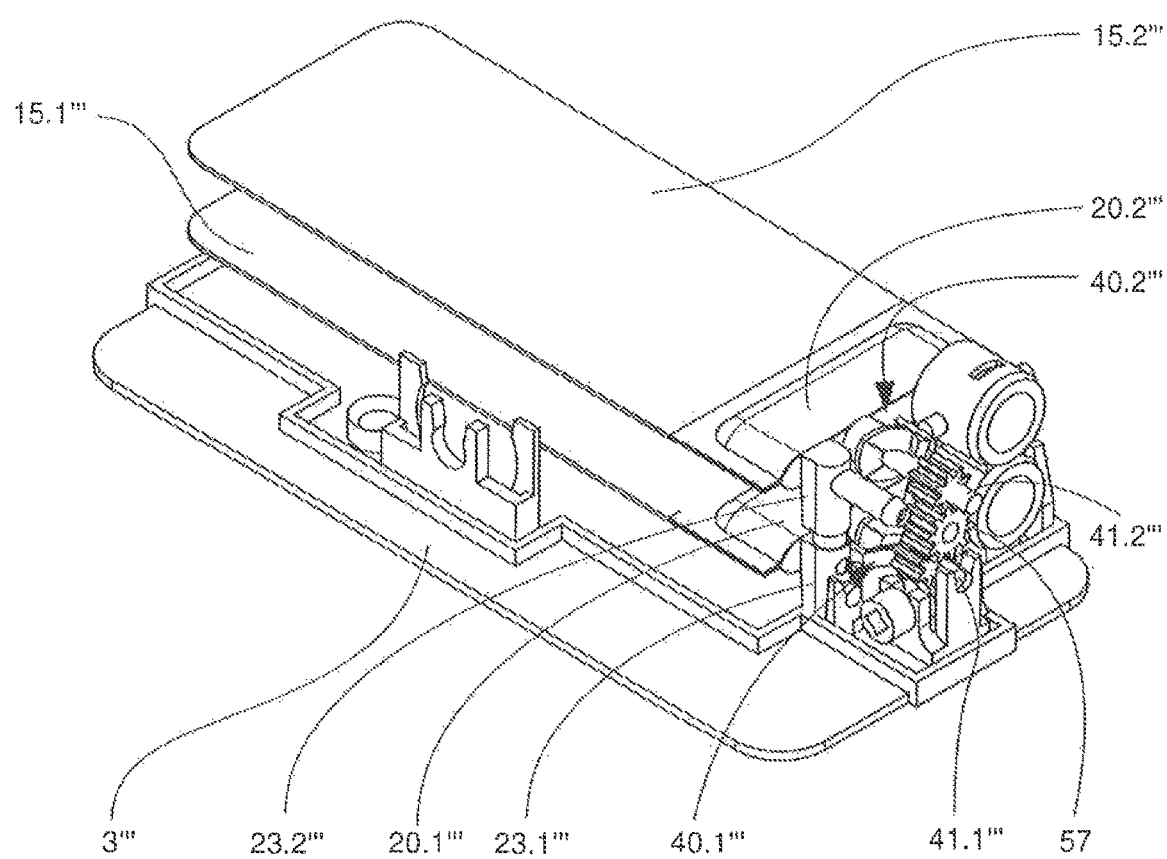
FIG. 36 shows an arrangement of a device according to the invention with multiple separate containers.

Finally, FIG. 36 shows a further arrangement for a device according to the invention, in which multiple separate containers 15.1'" and 15.2'" are used. The containers 15.1'" and 15.2'" each have a closure piece 20.1'" and 20.2'", which are formed analogously to the closure piece 20 of the device 1. The containers 15.1'" and 15.2'" are arranged stacked one on top of the other on a base plate 3'". Here, dispensing ports 23.1'" and 23.2'" are fluidically coupled to one another. Each container is assigned a wobble piston pump 40.1'" and 40.2'". Pistons 41.1'" and 41.2'" of the wobble piston pumps 40.1'" and 40.2'" are coupled to one another by way of a coupling gearwheel 57. In this way, only one of the pistons 41.1'" needs to be driven by a rotary drive.

Figure 37:
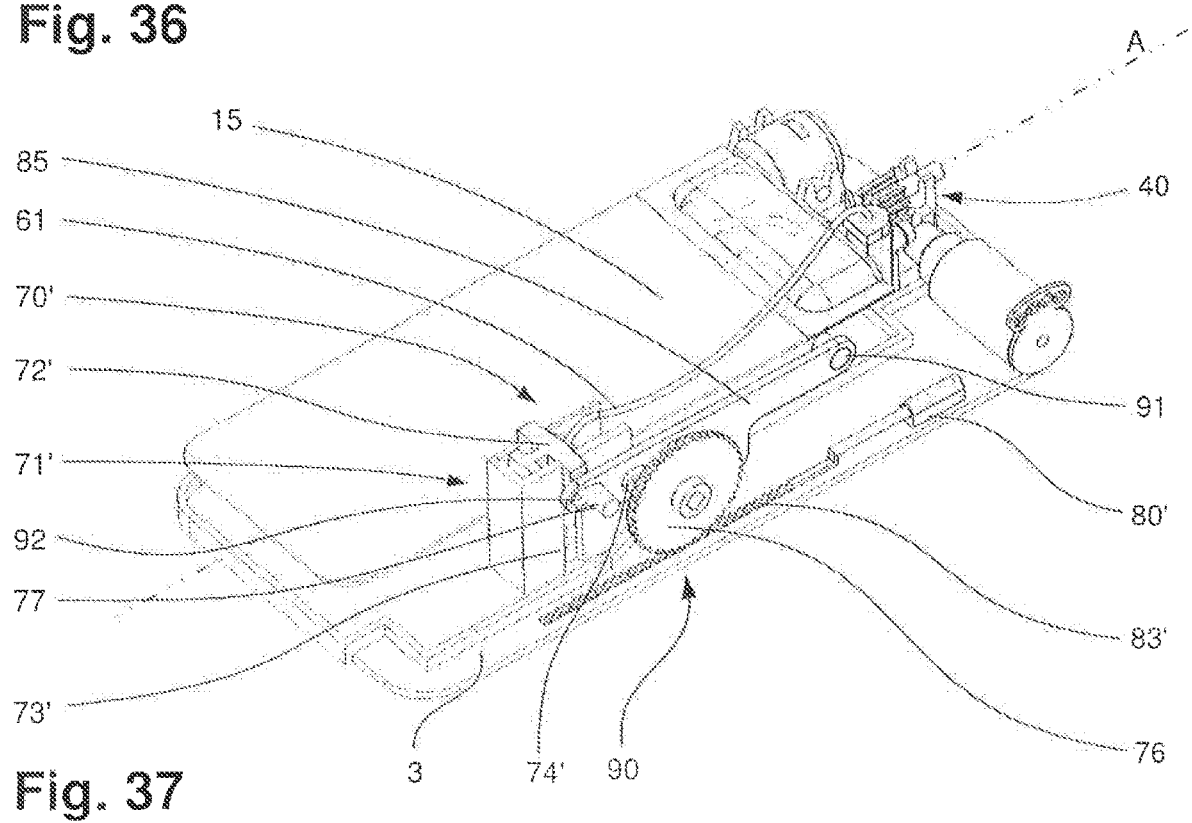
FIG. 37 shows a further embodiment of a device according to the invention, with a linear drive as an application drive, in an oblique partial view without a housing.

FIG. 37 shows a further embodiment of a device according to the invention in an oblique partial view without a housing. Container 15 and wobble piston pump 40 are designed analogously to those in the embodiment 1, for example of FIGS. 1 to 9. By contrast thereto, an application device 70' and an application drive 80' are designed as described below. The application device 70' is situated in a readiness position.

The application device 70' has a guide device 71' with a runner 72', which is mounted on guide rails 73' so as to be guided displaceably perpendicularly to the base plate 3. The runner 72' is arranged fixedly on the puncture cannula, which is in the form of a hollow needle 61, at the distal end region 65 thereof. The hollow needle 61 and the indwelling cannula 67 supported thereon are designed substantially analogously to those in the device 1.

The runner 72' has a cam 77 which is arranged fixedly on the runner 72' and which projects into a region of the drive module 6. An application gearing 90 and the application drive 80' are formed in the drive module 6 (housing not illustrated). The application drive 80' is in the form of a linear drive and has at least one electromagnetic coil (solenoid). Projecting into the solenoid there is a toothed rack 83' which interacts with the solenoid such that, when the solenoid is activated, a longitudinal displacement of the toothed rack 83' can be triggered. Here, the toothed rack 83' is arranged substantially parallel to A in the drive unit 6.

Here, the toothed rack 83' is in engagement with a circumferential toothed ring of a rotary disk 76' of the application gearing 90. The rotary disk 76' is mounted on a bearing bracket 94 (see for example FIG. 38) of the base plate 4' of the drive module 6 so as to be rotatable about an axis of rotation perpendicular to A and parallel to the base plate 3. It is thus possible, during a displacement of the toothed rack 83', for a rotation of the rotary disk 76' about the axis of rotation thereof to be effected. The rotary disk 76' has a cam 75' which is attached fixedly thereto and which is directed toward the application device 70'.

On a bearing bracket 93 of the base plate 4' of the drive module 6 (see for example FIG. 38), a lever arm 85 of the application gearing 90 is pivotably mounted on a pivot bearing 91. The lever arm 85 extends, substantially parallel to A, rearward from a front region of the device, that is to say a region arranged at the wobble piston pump 40 in the longitudinal direction A, to the guide device 71' of the application device 70. On the lever arm 85 there is formed a longitudinal guide 74' in the form of a slot, which is oriented with a slight inclination with respect to the puncturing direction D and into which the cam 75' of the rotary disk 76' engages. The cam 77 of the runner 72' in turn engages into a further longitudinal guide 92, which is in the form of a slot, of the lever arm 85. Here, the longitudinal guide 92 is arranged in an end region at a free longitudinal end of the lever arm 85. The cam 77 forms a coupling means by which the application gearing 90 can be coupled to the guide device 71'.

Figure 38:
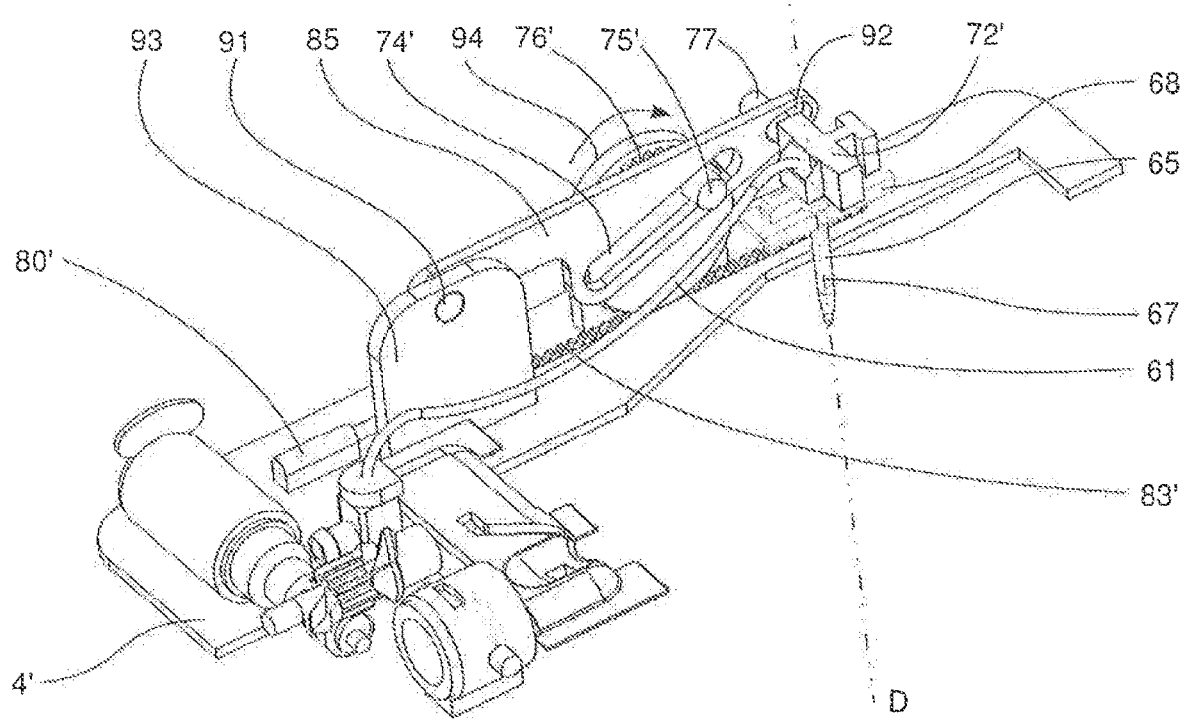
FIG. 38 shows a further partial view of the device of FIG. 37 in a readiness position on the application device.
Figure 39:
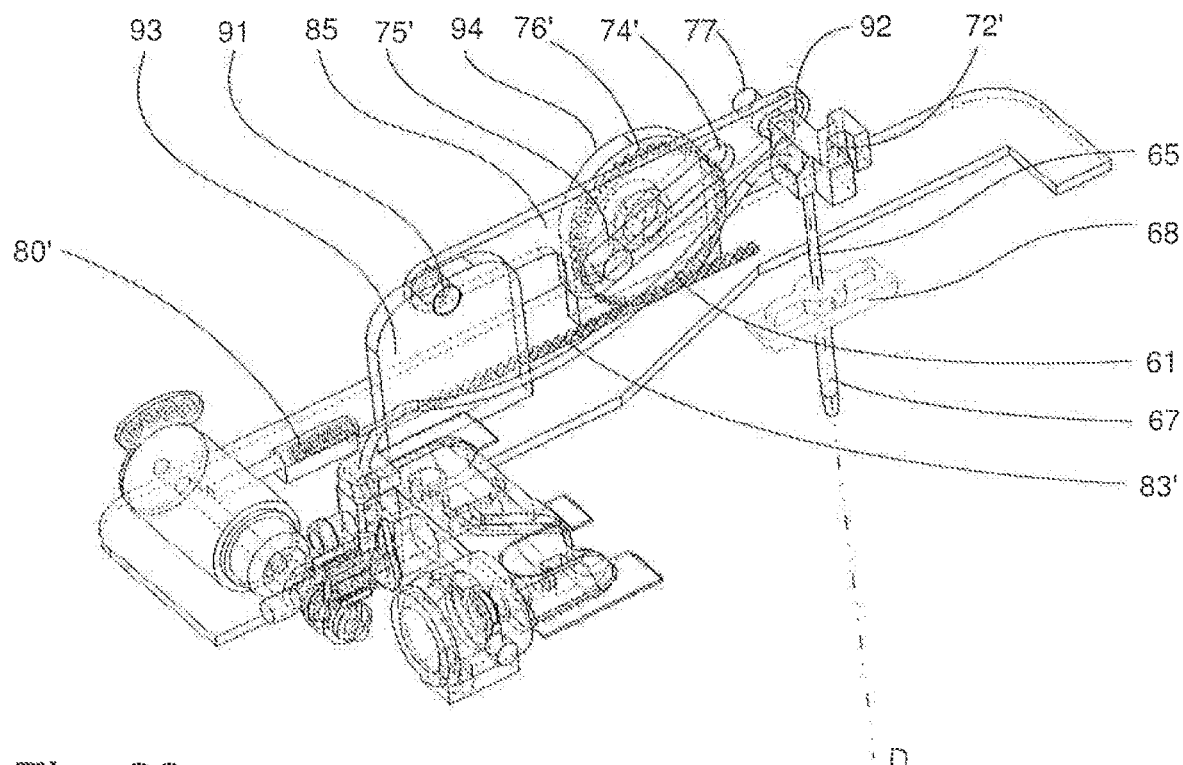
FIG. 39 shows a partial view as per FIG. 38 with the device in an end position on the application device.

FIG. 38 shows the device of FIG. 37 in a further partial view toward the application device 70' from the side of the container 15. The container 15 is not illustrated in order to give a clear view of the application device 70'. Likewise, for better clarity, the base plate 3 and further elements of the device are not illustrated. The application device 70' is situated in a readiness position. FIG. 39 shows an analogous view to FIG. 38, wherein the application device 70' is situated in the end position. FIGS. 38 and 39 will be described jointly below.

For the movement from the readiness position into the end position, the rotary disk 76' is set in rotation (see arrow) by way of the toothed rack 83'. Here, the cam 75' slides in the slot 74' and simultaneously exerts a force on the lever arm 85 toward the base plate 3. Here, the lever arm 85 is pivoted toward the base plate 3. By way of the slot 92, the lever arm 85 drives the cam 77 of the runner 72' along and displaces the runner 72' along the guide rails 73' toward the base plate 3. Here, the hollow needle 61 is, by way of its distal end region 65 and the indwelling cannula 67 supported thereon, deployed through the application opening 11 (not illustrated) into the application position (not illustrated). In the application position, the detent collar 68 of the indwelling cannula 67 engages with detent action on the detent collar 9 (not illustrated) as described in conjunction with FIGS. 10 and 11.

By way of further rotation of the rotary disk 76' in the same direction, the cam 75' reverses its movement direction parallel to the puncturing direction D, whereby the lever arm 85 is pivoted away from the base plate 3 again. By way of the cam 77, the runner 72' is thus displaced in the guide rails 73' away from the base plate 3. Here, the distal end region 65 is retracted, wherein the indwelling cannula 67 remains in the applied position. The application device 70' is thus in the end position (see FIG. 39). The inclination of the longitudinal guide 74' relative to the puncturing direction D permits a situation in which the retraction requires less of a rotation of the rotary disk 76' than the deployment. The rotary disk 76' thus only has to be rotated in one direction both for the deployment and for the retraction of the hollow needle 61. In this way, the linear drive 80' for moving the toothed rack 83' can be designed to have only one direction of movement.

Figure 40:
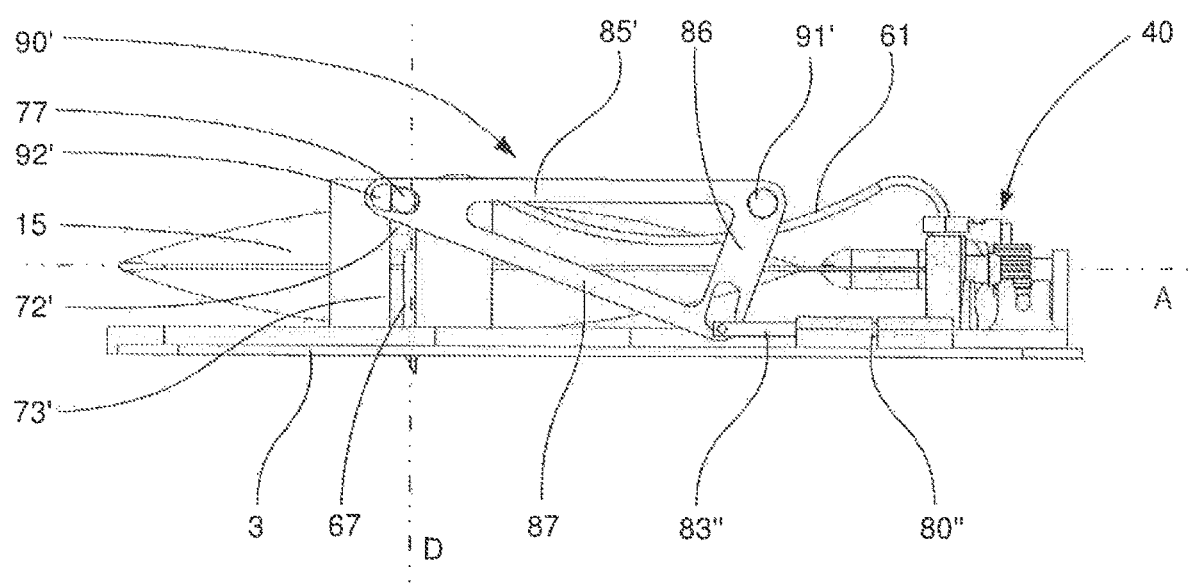
FIG. 40 shows a further embodiment of a device according to the invention, with a linear drive as an application drive, in a partial view, without a housing, from a side elevation.

FIG. 40 shows a further embodiment of a device according to the invention in a partial view, without a housing, from a side elevation. The container 15 and the wobble piston pump 40 are designed analogously to the embodiment 1, for example of FIGS. 1 to 9. The device of FIG. 40 has the same guide device 71' as the device of FIGS. 37 to 39, in particular comprising the runner 72', the guide rails 73' and the cam 77. By contrast, an application gearing 90' and an application drive 80" are designed as described below.

The application drive 80" has two solenoids by means of which a thrust rod 83", which is arranged parallel to the longitudinal direction A, can be moved rectilinearly in both directions. The application gearing 90' comprises a lever arm 85' which, substantially analogously to the lever arm 85, is pivotably mounted on a pivot bearing 91' on a bearing block (not illustrated) of the base plate 4' of the drive module 6. Likewise analogously to the lever arm 85, the lever arm 85' has a slot 92' which is engaged into by the cam 77, which is fixedly connected to the runner 72' of the guide device 71'. Thus, analogously to the device of FIGS. 37 to 39, the runner 72' is displaced toward the base plate 3 during a pivoting of the lever arm 85' toward the base plate 3, and is displaced away from the base plate 3 during a pivoting movement away from the latter. As described in conjunction with FIGS. 37 and 39, a deployment and retraction of the distal end region 65 of the hollow needle 61 through the application opening 11 (not illustrated) for the purposes of applying the indwelling cannula 67 are realized in this way.

The lever arm 85' has, in the manner of knee lever, an arm projection 86 which extends from the pivot bearing 91' toward the base plate 3. The lever arm 85' and arm projection 86 are rigidly connected to one another and enclose an angle such that, when a force acts on a free longitudinal end of the arm projection 86, the lever arm 85' can be pivoted about the pivot bearing 91'. The angle enclosed may in this case preferably amount to approximately 60 to 120 degrees in order to achieve an advantageous transmission of force from the arm projection 86 to the lever arm 85'. The free longitudinal ends of the lever arm 85' and of the arm projection 86 are, for better mechanical stability, connected to one another by way of a stiffening beam 87.

The thrust rod 83" of the application drive 80" acts in the region of the free longitudinal end of the arm projection 86, wherein the point of engagement is displaceable relative to the arm projection 86. It is achieved in this way that a relative displacement owing to the linear movement of the thrust rod 83" and the pivoting movement of the arm projection 86 can be compensated.

It is readily apparent that, in the case of a pulling movement of the thrust rod 83", the lever arm 85' is, by way of the arm projection 86, lowered toward the base plate 3, and in the case of a pushing movement, said lever arm can be raised in the opposite direction away from the base plate 3. The device as per FIG. 40 thus has an application device 70''' in the case of which no rotary disk is used, but rather a rectilinear movement is, by way of a knee lever (lever arm 85', arm projection 86), converted directly into a movement in the puncturing direction D.

The invention claimed is:

1. A device for dispensing a fluid comprising a container for accommodating the fluid, the device having a housing which, on an outside, has a contact surface by way of which the device can be affixed to a body of the patient,
wherein an injection device is provided which has a flexible transcutaneous indwelling cannula supported by a distal end region of a puncture cannula,
the puncture cannula is arranged in a readiness position within the housing and, during application of the indwelling cannula, said puncture cannula can, with the distal end region of the puncture cannula, be deployed out of the housing into an application position, and again retracted into an end position, through an application opening on the contact surface,
a proximal end region of the puncture cannula is connected in a fluid-tight fashion to a dispensing opening at which the fluid can be dispensed from the container,
a guide device is provided on which the distal end region of the puncture cannula is guided during the retraction and deployment through the application opening,
the puncture cannula is made of one piece comprising a central region between the proximal end region and a puncturing region having a puncturing tip and the puncturing region being located at the distal end region of the puncturing cannula, and
the proximal end region of the puncture cannula is arranged in a positionally fixed and rigid fashion in the device;
and wherein the central region of the puncture cannula, between the distal end region and the proximal end region of said puncture cannula at least in a readiness position, has a sag in the direction of the contact surface; and wherein the central region of the puncture cannula is stretched and forms a reduced curvature in the application position, in relation to the readiness position.

2. The device according to claim 1, wherein the guide device has a runner which is rigidly connected to the puncture cannula and which is guided by guide rails of the guide device.

3. The device according to claim 1, wherein the distal end region of the puncture cannula is of rectilinear form, and the guide device is in a form of a linear guide.

4. The device according to claim 3, wherein the proximal end region of the puncture cannula is oriented substantially parallel to the distal end region of the puncture cannula.

5. The device according to claim 1, wherein the puncture cannula, at least in the readiness position, is curved in a central region between the proximal end region of the puncture cannula and the distal end region of the puncture cannula.

6. The device according to claim 1, wherein a first angle enclosed between the proximal end region of the puncture cannula and an adjacent section of the central region of the puncture cannula, and a second angle enclosed between the distal end region of the puncture cannula and an adjacent section of the central region of the puncture cannula are each less than 90 degrees.

7. The device according to claim 1, wherein the indwelling cannula as a whole is arranged so as to be displaceable in the distal end region of the puncture cannula, and the indwelling cannula, in a proximal end region of the indwelling cannula, surrounds the puncture cannula in fluid-tight fashion.

8. The device according to claim 1, wherein the indwelling cannula can be arrested on the housing when the puncture cannula is in the application position.

9. The device according to claim 1, wherein an application drive is provided, by which the distal end region of the puncture cannula can be deployed and again retracted by way of an application gearing.

10. The device according to claim 9, wherein the application drive comprises a rotary drive, and the application gearing comprises a worm gearing, wherein the rotary drive can be or is coupled to the puncture cannula.

11. The device according to claim 9, wherein the application drive comprises a linear drive and the application gearing comprises a pivotably mounted knee lever wherein the linear drive can be or is coupled to the puncture cannula.

12. The device according to claim 9, wherein the application gearing has a longitudinal guide, which is arranged transversely with respect to the puncturing direction and into which a cam of the application gearing engages so that the cam is displaceable in the longitudinal guide.

13. The device according to claim 1, wherein the puncture cannula is arranged so as to allow for a puncturing movement perpendicular to a surface of the skin.

14. The device according to claim 1, wherein the retraction and deployment of the puncture cannula through the application opening is contact free.

15. The device according to claim 1, wherein a base plate forms the contact surface of the device, and a dispensing port is oriented perpendicular to and extends away from the base plate.

16. A device for dispensing a fluid comprising a container for accommodating the fluid, the device having a housing which, on an outside, has a contact surface by way of which the device is affixable to a body of the patient,
wherein an injection device is provided which has a flexible transcutaneous indwelling cannula supported by a distal end region of a puncture cannula,
the puncture cannula is arranged in a readiness position within the housing and, during application of the indwelling cannula, said puncture cannula can, with the distal end region of the puncture cannula, be deployed out of the housing into an application position, and again retracted into an end position, through an application opening on the contact surface,
a proximal end region of the puncture cannula is connected in a fluid-tight fashion to a dispensing opening at which the fluid can be dispensed from the container,
a guide device is provided by which the distal end region of the puncture cannula is guided during deployment and retraction through the application opening,
the puncture cannula comprises a monolithic structure comprising a central region between the proximal end region and a puncturing region having a puncturing tip and the puncturing region being located at the distal end region of the puncturing cannula, and
the proximal end region of the puncture cannula is arranged in a positionally fixed and rigid fashion in the device and the central region of the puncture cannula has, at least in a readiness position, a sag formed in the direction of the contact surface;
and wherein the central region of the puncture cannula is stretched, and forms a reduced curvature in the application position, and wherein the distal end region of the puncture cannula comprises a hollow needle which is made of steel.

* * * * *